(12) United States Patent
Shin et al.

(10) Patent No.: US 9,745,971 B2
(45) Date of Patent: Aug. 29, 2017

(54) ELECTROOSMOTIC PUMP AND FLUID PUMPING SYSTEM INCLUDING THE SAME

(71) Applicant: SOGANG UNIVERSITY RESEARCH FOUNDATION, Seoul (KR)

(72) Inventors: Woonsup Shin, Seoul (KR); Enhua Zhu, Seoul (KR)

(73) Assignee: SOGANG UNIVERSITY RESEARCH FOUNDATION (KR)

( * ) Notice: Subject to any disclaimer, the term of this patent is extended or adjusted under 35 U.S.C. 154(b) by 0 days.

(21) Appl. No.: 15/054,683

(22) Filed: Feb. 26, 2016

(65) Prior Publication Data

US 2016/0177931 A1 Jun. 23, 2016

Related U.S. Application Data

(63) Continuation of application No. PCT/KR2014/007933, filed on Aug. 26, 2014.

(30) Foreign Application Priority Data

Aug. 26, 2013 (KR) .......................... 10-2013-0101334
Aug. 27, 2013 (KR) .......................... 10-2013-0101641

(51) Int. Cl.
*F04B 17/03* (2006.01)
*A61K 9/00* (2006.01)
(Continued)

(52) U.S. Cl.
CPC ............ *F04B 17/03* (2013.01); *A61K 9/0004* (2013.01); *A61M 5/142* (2013.01); *A61M 5/145* (2013.01);
(Continued)

(58) Field of Classification Search
CPC ......... A61M 2005/14204; A61M 2005/14513; A61M 5/142; A61M 5/145; F04B 17/03;
(Continued)

(56) References Cited

U.S. PATENT DOCUMENTS 4,933,106 A 6/1990 Sakai et al.
8,482,839 B2 7/2013 Zaghib et al.
(Continued)

FOREIGN PATENT DOCUMENTS

CN 87108059 A 6/1988
CN 101971086 A 2/2011
(Continued)

OTHER PUBLICATIONS

Spanninga (The Characterization and Fabrication of Poly (3,4-Ethylenedioxythiophene) Enzyme Based Biosensors, 2010).*
(Continued)

*Primary Examiner* — Dominick L Plakkoottam
(74) *Attorney, Agent, or Firm* — Riverside Law LLP

(57) ABSTRACT

A fluid pumping system may include an electroosmotic pump; and a separation member provided at least one end of the electroosmotic pump, and configured to separate the fluid and a transfer target fluid. The electroosmotic pump may include: a membrane that allows a fluid to move therethrough; and a first electrode and a second electrode which are respectively provided at two opposite sides of the membrane, and each of which is formed of a porous material or has a porous structure to allow a fluid to move therethrough; each of the first electrode and the second electrode may contain a conductive polymer in which an anionic polymer is included or may be made of porous carbon only; and an electrochemical reaction of the first electrode and the second electrode may take place as a cation is moved in a direction whereby a charge balance is established.

17 Claims, 27 Drawing Sheets

(51) Int. Cl.
*A61M 5/142* (2006.01)
*A61M 5/145* (2006.01)
*F04B 19/00* (2006.01)
*B01D 61/42* (2006.01)

(52) U.S. Cl.
CPC . *F04B 19/006* (2013.01); *A61M 2005/14204* (2013.01); *A61M 2005/14513* (2013.01); *B01D 61/427* (2013.01); *B01L 2400/0418* (2013.01)

(58) Field of Classification Search
CPC ...... F04B 19/006; F04B 17/00; F04B 43/067; A61K 9/0004; B01L 2400/0418; B01L 2200/027; B01L 3/5027; B01D 61/427
See application file for complete search history.

(56) References Cited

U.S. PATENT DOCUMENTS

| | | | | |
|---|---|---|---|---|
| 2005/0230080 | A1* | 10/2005 | Paul | F04B 19/006 165/47 |
| 2008/0260542 | A1* | 10/2008 | Nishikawa | B01L 3/565 417/48 |
| 2009/0126813 | A1* | 5/2009 | Yanagisawa | F04B 19/006 137/831 |
| 2009/0260990 | A1* | 10/2009 | Yanagisawa | C04B 35/14 204/641 |
| 2010/0328841 | A1* | 12/2010 | Reinhoudt | C02F 1/46109 361/301.4 |
| 2011/0168558 | A1* | 7/2011 | Fransaer | C09D 5/024 204/477 |
| 2013/0041353 | A1* | 2/2013 | Shin | A61M 5/14248 604/892.1 |
| 2013/0153797 | A1* | 6/2013 | Puleo | B01L 3/50273 251/12 |
| 2013/0156615 | A1* | 6/2013 | Puleo | A61K 9/0004 417/410.1 |
| 2013/0276851 | A1* | 10/2013 | Crispin | H01L 35/28 136/201 |

FOREIGN PATENT DOCUMENTS

| | | |
|---|---|---|
| EP | 1 911 971 A1 | 4/2008 |
| JP | 2001-240730 A | 9/2001 |
| KR | 10-2009-0067149 A | 6/2009 |
| KR | 10-0946598 B1 | 3/2010 |
| KR | 10-2013-0075725 A | 7/2013 |

OTHER PUBLICATIONS

International Search Report of PCT/KR2014/007933 dated Nov. 27, 2014.

Kwon et al., "Porous Glass Electroosmotic Pumps Reduced Bubble Generation Using Reversible Redox Solutions", Transaction of the Korean Society of Mechanical Engineers B, 2012, vol. 36, No. 7, pp. 753-757.

Seo et al., "Basic Performance Test on Electroosmotic Pump with Porous Glass Slit", 2008 The Korean Society of Visualization, Journal of Fall Conference, 2008, pp. 36-39.

Seo et al., "Basic Performance Test on Electroosmotic Pump with Porous Glass Slit", The Korean Society of Visualization, Journal of Fall Conference, 2008, pp. 36-39.

Notice of Allowance dated Oct. 21, 2014, for Korean Application Serial No. 10-2013-0101334.

* cited by examiner

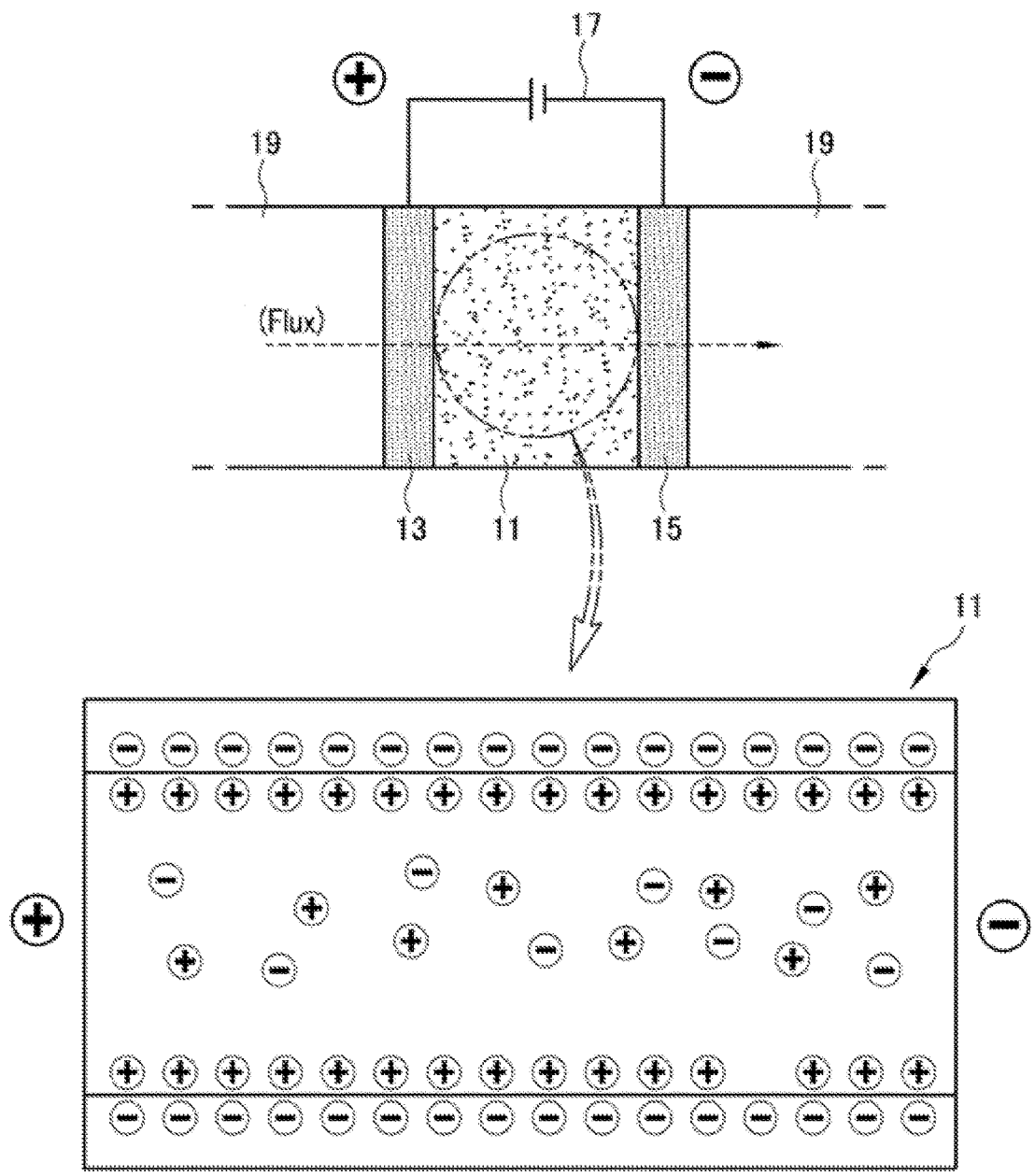

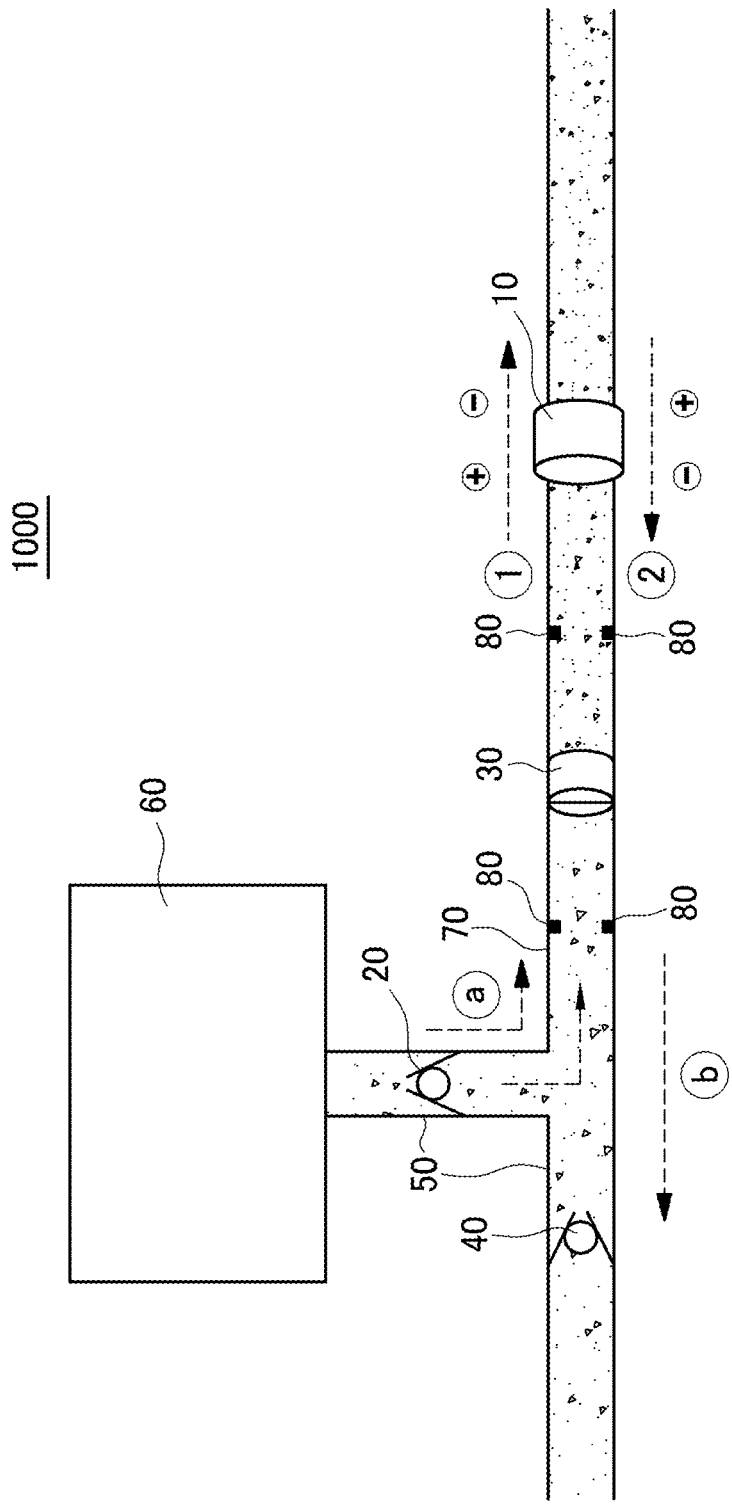

ELECTROOSMOTIC PUMP AND FLUID PUMPING SYSTEM INCLUDING THE SAME

CROSS-REFERENCE TO RELATED APPLICATION

This application claims priority from the PCT application No. PCT/KR2014/007933, filed on Aug. 26, 2014, the Korean Patent Application No. 10-2013-0101334, filed on Aug. 26, 2013, and the Korean Patent Application No. 10-2013-0101641, filed on Aug. 27, 2013, the entire disclosure of which is incorporated herein by reference in its entirety.

TECHNICAL FIELD

The various embodiments described herein pertain generally to an electroosmotic pump using an improved electrode, and a fluid pumping system using the electroosmotic pump.

BACKGROUND

An electroosmotic pump is a pump using a movement of a fluid by electro-osmosis which occurs when a voltage is applied to electrodes provided at two opposite ends of a capillary tube or a porous membrane.

Conventionally, platinum, which has high stability, has been widely used as a material of the electrodes. Recently, in order to drive the electroosmotic pump stably without accompanying gas generation, silver (Ag), silver oxide (AgO), MnO(OH), polyaniline (PANI), and the like are used as materials of the electrodes.

Among the materials used as the electrodes, a conductive polymer such as polyaniline is generally synthesized through polymerization whereby a monomer is oxidized electrochemically or chemically. Since the amount of positive charges within a polymer chain increases continuously during the polymerization, it is required to add negatively charged ions to the polymer chain so that the polymerization may progress continuously.

As the most general method of synthesizing a conductive polymer, a monomer such as aniline, pyrrole or thiophene is electrochemically oxidized or chemically oxidized by using an oxidizing agent in a solution of nitric acid ($HNO_3$) or hydrochloric acid (HCl). The synthesis of the conductive polymer progresses as anions (negative ions) (e.g., $NO_3^-$, $Cl^-$, or the like) that exist in the solution are continuously added to a polymer chain. That is, since the produced polymer chain itself is positively charged, the conductive polymer is synthesized as the anions are added to the polymer chain to establish a charge balance.

In this regard, Japanese Patent Laid-open Publication No. 2001-240730 (entitled "CONDUCTIVE POLYTHIOPHENE") discloses polythiophene which is doped with molecular anions such as bis(perfluoro alkanesulfonyl)imide.

If a voltage is applied to each of a (+) electrode and a (−) electrode containing the conductive polymer produced as stated above, an oxidation-reduction reaction takes place in the entire polymer matrix, breaking a charge balance. Accordingly, to balance charges again, an ion having high mobility moves into the conductive polymer. By way of example, if polyaniline (PANI) is synthesized in a solution of nitric acid ($HNO_3$), a polymer containing a molecular anion of $NO_3^-$ is produced. If the polyaniline (PANI) in the form of an emeraldine salt (refer to Reaction Formula 1 below) containing this small molecular anion, positive (+) charges in the polymer chain disappear. Accordingly, to establish a charge balance, the anion $NO_3^-$ once added to the polymer chain ($A^-$ in the following Reaction Formula 1) comes out of the polymer chain. As a result, the polyaniline (PANI) is converted into the form of a leucoemeraldine base and becomes a neutral polymer chain.

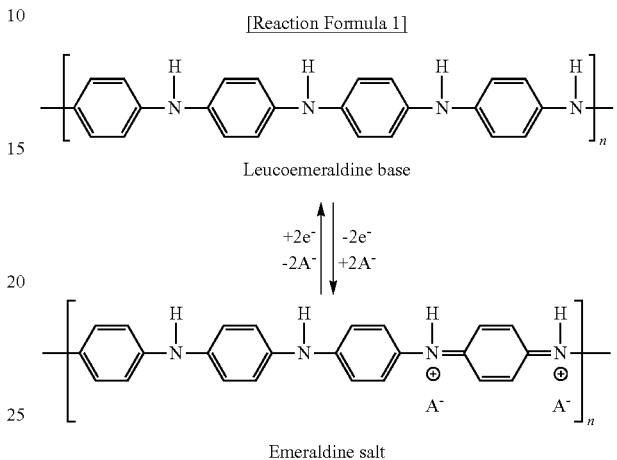

[Reaction Formula 1]

Leucoemeraldine base

Emeraldine salt

As stated above, in the oxidation-reduction reaction, the anion that has come out of the polymer chain for a charge balance of the conductive polymer contained in any one of the electrodes is moved to establish a charge balance of the conductive polymer of the other electrode. If a moving velocity of such an ion is slow, the oxidation-reduction reaction of the electrodes may not occur smoothly.

In case that an electrode reaction takes place in a solution which hardly contains electrolyte, it is difficult that the small anion ($NO_3^-$, $Cl^-$, or the like) once moved into the conductive polymer of one electrode is mixed into the conductive polymer of the other electrode after coming out of the conductive polymer of the one electrode. Since the electroosmotic pump is mostly operated in a solution having a low concentration of electrolyte, if a material containing an anion having high mobility is used as an electrode, it is difficult to expect an electrode reaction to progress continuously. As a result, performance of the electroosmotic pump would be sharply deteriorated.

Further, generally, silica, glass, or the like is used as a material of a porous membrane included in the electroosmotic pump. A surface of the porous membrane made of these materials is negatively charged in an aqueous solution. Here, the anion that has come out of the conductive polymer during the aforementioned oxidation-reduction reaction of the electrodes should pass through the porous membrane to be moved between the electrodes. Since however, the surface of the porous membrane is negatively charged, a repulsive force is applied between the anion and the porous membrane, so that it is difficult for the anion to flow through the porous membrane. Therefore, the oxidation-reduction reaction of the electrodes may not take place smoothly, resulting in deterioration of the performance of the electroosmotic pump.

Meanwhile, as one of basic structures of an electrode, there is known a structure in which an electrode material as mentioned above (i.e., silver (Ag), silver oxide (AgO), MnO(OH), polyaniline, etc.) is electrodeposited on a carbon paper. Conventionally, by using this structure, a pumping force is generated by moving a fluid through an oxidation-reduction reaction of the material electrodeposited on the electrode.

In this regard, International Patent Laid-open Publication No. WO2011-112723 (entitled "ELECTRO-OSMOTIC PUMPS, SYSTEMS, METHODS, AND COMPOSITIONS") describes an electroosmotic pump including electrodes on which silver (Ag) and silver oxide (AgO) are electrodeposited, respectively.

In case of the conventional electrodes, however, since a process of electrodepositing the other materials on the carbon paper is required, the whole process of preparing the electroosmotic pump has been complicated.

SUMMARY

Example embodiments of the present disclosure provide an electroosmotic pump including an electrode in which an electrochemical reaction takes place smoothly and a manufacturing process of which is not complicated, and also provide a fluid pumping system using the electroosmotic pump.

However, the problems sought to be solved by the present disclosure are not limited to the above description and other problems can be clearly understood by those skilled in the art from the following description.

In accordance with an exemplary embodiment of the present disclosure, there is provided an electroosmotic pump. The electroosmotic pump may include: a membrane that allows a fluid to move therethrough; and a first electrode and a second electrode which are respectively provided at two opposite sides of the membrane, and each of which is formed of a porous material or has a porous structure to allow a fluid to move therethrough. Herein, each of the first electrode and the second electrode may contain a conductive polymer in which an anionic polymer is included, and an electrochemical reaction of the first electrode and the second electrode may take place as a cation is moved in a direction whereby a charge balance is established.

In accordance with another exemplary embodiment of the present disclosure, there is provided a fluid pumping system. The system may include: the electroosmotic pump according to an exemplary embodiment of the present disclosure, and a separation member provided at least one end of the electroosmotic pump, and configured to separate the fluid and a transfer target fluid.

In accordance with yet another exemplary embodiment of the present disclosure, there is provided an electroosmotic pump. The electroosmotic pump may include: a membrane that allows a fluid to move therethrough; and a first electrode and a second electrode which are respectively provided at two opposite sides of the membrane, and each of which is formed of a porous material or has a porous structure to allow a fluid to move therethrough. Herein, each of the first electrode and the second electrode may be made of porous carbon only, and an electrochemical reaction of the first electrode and the second electrode may take place through an electrochemical reaction of the porous carbon itself.

In accordance with yet another exemplary embodiment of the present disclosure, there is provided a fluid pumping system. The system may include: the electroosmotic pump according to yet another exemplary embodiment of the present disclosure; and a separation member provided at least one end of the electroosmotic pump, and configured to separate the fluid and a transfer target fluid.

According to the example embodiments, a conductive polymer in which anionic polymer is mixed is used as a material of the first electrode and the second electrode, and cations (positive ions) are moved during an electrochemical reaction of the first and second electrodes. Accordingly, a velocity of the electrochemical reaction of the electrodes can be improved, so that performance of the electroosmotic pump can be ameliorated.

Furthermore, according to the example embodiments, the first electrode and the second electrode are made of porous carbon only, and a pumping force is generated through an electrochemical reaction of the porous carbon itself. Accordingly, a process of electrodepositing another material on the electrodes is not required, and, thus, the electroosmotic pump can be simply produced.

BRIEF DESCRIPTION OF THE DRAWINGS

FIG. 2 is a diagram for describing an operation of the electroosmotic pump according to the first example embodiment.

FIG. 6 is a configuration view of a fluid pumping system according to the first example embodiment.

DETAILED DESCRIPTION

Figure 1:
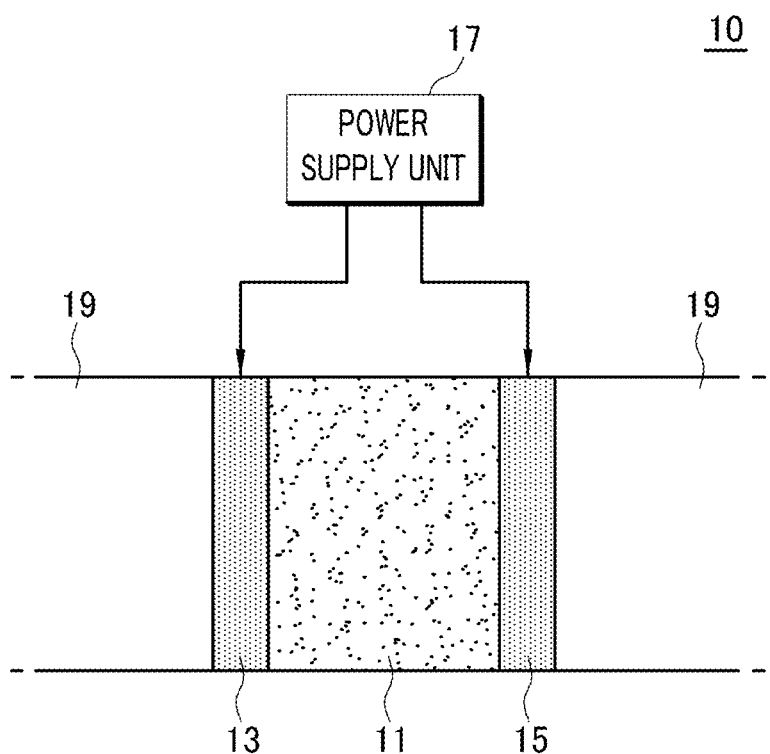
FIG. 1 is a configuration view of an electroosmotic pump according to a first example embodiment.

Hereinafter, example embodiments will be described in detail so that inventive concept may be readily implemented by those skilled in the art. However, it is to be noted that the present disclosure is not limited to the example embodiments and examples but can be realized in various other ways. In drawings, parts not directly relevant to the description are omitted to enhance the clarity of the drawings, and like reference numerals denote like parts through the whole document.

Through the whole document, the term "on" that is used to designate a position of one element with respect to another element includes both a case that the one element is adjacent to the another element and a case that any other element exists between these two elements.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise. Further, through the whole document, the term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from the group consisting of components, steps, operation and/or elements described in Markush type and thereby means that the disclosure includes one or more components, steps, operations and/or elements selected from the Markush group.

Hereafter, example embodiments of the present disclosure will be described in detail with reference to the accompanying drawings, which form a part of the description.

[Electroosmotic Pump Including a Conductive Polymer Electrode and Fluid Pumping System]

First, an electroosmotic pump 10 according to a first example embodiment will be discussed.

FIG. 1 is a configuration view of the electroosmotic pump 10 according to the first example embodiment.

The electroosmotic pump 10 includes a membrane 11; and a first electrode 13 and a second electrode 15 respectively provided at two opposite sides of the membrane 11. The first electrode 13 and the second electrode 15 are connected to a power supply unit 17.

The membrane 11 is provided in a fluid path 19 through which a fluid moves. The membrane 15 is made of a porous material or has a porous structure to allow a fluid to move therethrough.

The first electrode 13 and the second electrode 15 are provided at the two opposite sides of the membrane on the fluid path 19. Each of the first electrode 13 and the second electrode 15 contains a conductive polymer in which anionic polymer is mixed. The first electrode 13 and the second electrode 15 are maintained spaced apart from each other at a regular interval with the membrane 11 therebetween. Like the membrane 11, each of the first electrode 13 and the second electrode 15 is also made of a porous material or has a porous structure to allow a fluid to flow therethrough.

The power supply unit 17 is connected to the first electrode 13 and the second electrode 15, and is configured to supply a power to the first electrode 13 and the second electrode 15 so that an electrochemical reaction may take place. The electrochemical reaction of the first electrode 13 and the second electrode 15 occurs as cations (positive ions) are moved.

To elaborate, the power supply unit 17 is configured to supply a voltage to the first electrode 13 and the second electrode 15 while reversing a polarity of the voltage alternately. Here, the term "supplying a voltage while reversing a polarity of the voltage alternately" means supplying an electric current in opposite directions alternately.

Accordingly, in the electroosmotic pump 10, through the movement of the fluid, a pumping force can be generated, and, at the same time, consumption and reproduction of the first electrode 13 and the second electrode 15 are performed repeatedly.

By way of non-limiting example, the power supply unit 17 includes a DC power supply device (not shown) configured to supply a DC voltage to each of the first electrode 13 and the second electrode 15. Further, the power supply unit 17 may also include a voltage direction switching device (not shown) configured to switch a polarity of the DC voltage supplied to each of the first electrode 13 and the second electrode 15 alternately at a preset time interval.

Through the above-described configuration, it is possible to continuously reverse the polarity of the voltage applied to each of the first electrode 13 and the second electrode 15 at the preset time interval.

The fluid path 19 provides a moving path of the fluid which moves between two opposite sides (spaces) with the membrane 11 and the first and second electrodes 13 and 15 therebetween.

Here, the fluid path 19 may be in the form of a vessel which is filled with the fluid. By way of example, the fluid path 19 may have a cylinder shape, but not limited thereto.

Further, the fluid may also be charged in the membrane 11 and the first and second electrodes 13 and 15 as well as in the fluid path 19.

Furthermore, the fluid path 19 may have an opening for the transmission of a pumping force. For example, the opening may be formed in either one or both of two opposite spaces separated by the membrane 11, the first electrode 13 and the second electrode 15, to thereby transmit the pumping force generated by the movement of the fluid to the outside. For instance, the opening formed at the fluid path 19 may be connected to a pumping line 70 of a fluid pumping system 1000 depicted in FIG. 6, so that the pumping force can be transmitted to the outside.

FIG. 2 is a diagram for describing an operation of the electroosmotic pump according to the first example embodiment, and FIG. 3 is a diagram for describing a reversible electrode response of the electroosmotic pump according to the first example embodiment.

Referring to FIG. 2 and FIG. 3, an operation of the electroosmotic pump 10 according to the first example embodiment will be explained.

If a power is supplied to the first electrode 13 and the second electrode 15 by the power supply unit 17, a voltage difference is generated between the first electrode 13 and the second electrode 15.

Due to the voltage difference between the first electrode 13 and the second electrode 15, an oxidation-reduction reaction takes place in the first electrode 13 and the second electrode 15, so that a charge balance is broken. At this time, as ions which have high mobility are moved, the charge balance is achieved.

Here, if a voltage is applied to each of the first electrode 13 and the second electrode 15, an oxidation-reduction reaction occurs in the first electrode 13 and the second electrode 15, and ions are moved through the membrane 11, so that the fluid can also be moved.

The membrane 11 allows not only the fluid but also ions to move therethrough. If the power supply unit 17 is connected to the electrodes 13 and 15, the fluid and the ions can be moved from one side of the membrane 11 to the other side, or vice versa. As the fluid and the ions are moved through the membrane 11 in this way, a pumping force is generated.

As an example, the membrane 11 may be formed by using silica, glass or the like which is in the form of granules having a size ranging from about 0.1 µm to about 5 µm, but not limited thereto.

Further, for instance, the membrane 11 may be a disc membrane, or a MEA (membrane electrode assembly). Besides these mentioned examples, the membrane 11 may also be formed of various porous materials or may have various porous structures.

Each of the first electrode 13 and the second electrode 15 contains a conductive polymer in which an anionic polymer is mixed. An electrochemical reaction of the first electrode 13 and the second electrode 15 occurs as cations (positive ions) are moved in a direction whereby a charge balance is established. Here, either of the first electrode 13 and the second electrode 15 generates cations through the electrochemical reaction, whereas the other of the first electrode 13 and the second electrode 15 consumes the cations through the electrochemical reaction.

For example, the cations generated and consumed during the electrochemical reaction of the first electrode 13 and the second electrode 15 may be monovalent cations, but not limited thereto.

By way of non-limiting example, the cations may include hydrogen ions ($H^+$), but not limited thereto.

An ionic mobility of $H^+$, which is proton, is much higher than those of other cations. As stated above, the electroosmotic pump 10 accompanies a movement of ions and a movement of a fluid. Accordingly, in case that the hydrogen ions are moved during the electrode reaction, a fluid transfer velocity would be increased, so that the performance of the electroosmotic pump 10 can be further ameliorated.

By way of non-limiting example, the electroosmotic pump 10 may use an aqueous solution as the fluid. By using the aqueous solution as the fluid, the hydrogen ions can be moved during the electrode reaction.

The electroosmotic pump 10 according to the first example embodiment of the present disclosure may exhibit higher pumping performance in a solution which hardly contains electrolyte. At this time, hydrogen ions which are cations generated by dissociation of water may be moved to establish a charge balance.

Further, depending on the fluid involved, the cations may include various ions such as $Na^+$ and $K^+$.

A conductive polymer is electrodeposited on the first electrode 13 and the second electrode 15.

Conventionally, to synthesize the conductive polymer, a method of electrochemically or chemically oxidizing a monomer such as aniline, pyrrole or thiophene in a solution of nitric acid ($HNO_3$) or hydrochloric acid (HCl) has been most widely employed. This synthesis process of the conductive polymer progresses as anions (negative ions) (e.g., $NO_3^-$, $Cl^-$, or the like) that exist in the solution are continuously added to a polymer chain to establish a charge balance.

If a voltage is applied to each of the electrodes containing the conductive polymer synthesized as stated above, molecular cations (e.g., $NO_3^-$, $Cl^-$, or the like) represented by $2A^-$ in the following Reaction Formula (2) are moved to achieve a charge balance.

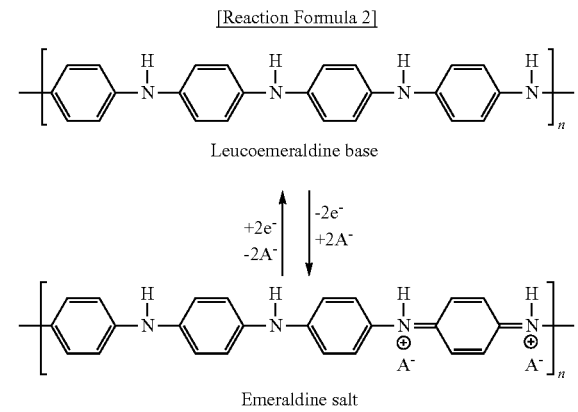

[Reaction Formula 2]

Leucoemeraldine base

Emeraldine salt

Meanwhile, silica, glass, or the like is generally used as a material of the porous membrane included in the electroosmotic pump. A surface of the porous membrane made of such a material is negatively charged in the aqueous solution.

The anions ($A^-$) that have come out of the conductive polymer for the charge balance are made to pass through the porous membrane. Since however, the surface of the porous membrane is negatively charged, a repulsive force is applied between the anions and the porous membrane, so that the anions cannot pass through the porous film smoothly. As a result, in the electrodes containing the conventional conductive polymer, an oxidation-reduction reaction could not occur rapidly, and thus, the fluid could not be moved rapidly.

Meanwhile, the electroosmotic pump 10 according to the example embodiment includes a conductive polymer (i.e., anionic polymer) containing large-size anions. Accordingly, since the anionic polymer is fixed and cannot be moved during an oxidation-reduction reaction of the electrodes 13 and 15, cations that exist in the solution are moved to establish a charge balance.

For example, when cationic polymer-anionic polymer are expressed as $—[P^-]_n—[S^-]_n—$, the oxidation-reduction reaction of the electrodes 13 and 15 are represented by the following Reaction Formula 3 and Reaction Formula 4.

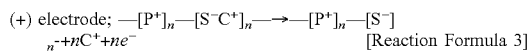

(+) electrode; $—[P^+]_n—[S^-C^+]_n—\rightarrow—[P^+]_n—[S^-]_n—+nC^++ne^-$  [Reaction Formula 3]

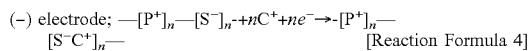

(−) electrode; $—[P^+]_n—[S^-]_n—+nC^++ne^-\rightarrow-[P^+]_n—[S^-C^+]_n—$  [Reaction Formula 4]

As can be seen from the above, during a reduction reaction of the (−) electrode, if a conductive polymer matrix becomes neutral ($P^+\rightarrow P$), cations ($C^+$) that exist in the solution are mixed in to establish a charge balance of the fixed anionic polymer ($S^-$).

That is to say, referring to FIG. 2, Reaction Formula 3 and Reaction Formula 4, the anionic polymer ($S^-$) is not moved and the cations ($C^+$) in the solution are moved during the oxidation-reduction reaction electrodes 13 and 15. Since an attraction force is applied between the cations and the negatively charged membrane 11, the cations can pass through the membrane 11 easily. Therefore, the oxidation-reduction reaction can take place at a high velocity.

That is, in the electroosmotic pump 10 according to the first example embodiment, the conductive polymer containing the anions in the form of the large-size polymer, not small mobile anions, is electrodeposited on the electrodes 13 and 15. Accordingly, during the oxidation-reduction reaction of the electrodes 13 and 15, the small cations in the solution are moved instead of the anions in the form of the large-size polymer. Since these anions can easily pass through the negatively charged membrane 11, the velocity of the electrochemical reaction of the electrode 13 and 15 can be improved. Thus, the fluid can be moved smoothly, so that the effective and stable electroosmotic pump 10 can be achieved.

This inventive conductive polymer can be produced through polymerization of a monomer in a solution containing an anionic polymer.

For example, if the monomer is oxidized in the solution containing the anionic polymer, the anionic polymer that exists in the solution is mixed in, and the polymerization progresses. Accordingly, a polymer complex composed of anionic polymer-cationic polymer can be produced.

For example, the conductive polymer can be synthesized through electrochemical oxidation, or chemical oxidation using an oxidizing agent.

By way of non-limiting example, the conductive polymer may include one selected from the group consisting of polyaniline, polypyrrole, polythiophene, polythionine, quinone polymer, derivatives thereof, and combinations thereof, but not limited thereto.

Besides the aforementioned examples, the conductive polymer may be implemented by any of various kinds of polymers having high electrical conductivity.

By way of non-limiting example, the anionic polymer may include one selected from the group consisting of polystyrene sulfonate, SPEEK (sulfonated-polyetheretherketone), polyacrylate, polyvinylphosphonate, polyoxometalate, nafion, derivatives thereof, and combinations thereof, but not limited thereto.

Here, the nafion refers to a polymer prepared by introducing a sulfuric acid group into an architecture of poly (tetrafluoroethylene).

Besides, the anionic polymer may be implemented by any of various polymers which are negatively charged. For example, the anionic polymer may include a complex synthesized with a neutral polymer, such as polyethylene glycol or polyacrylamide, but not limited thereto.

Furthermore, for instance, the electrodes 13 and 15 may additionally include carbon nanostructures.

By way of example, but not limitation, the carbon nanostructures may include carbon nanotube (CNT), graphene, carbon nanoparticle, fullerene, graphite, and so forth.

In case of an electrode on which a complex of a conductive polymer containing a carbon nanotube among the carbon nanostructures, an oxidation-reduction reaction can take place more stably at a higher velocity. Detailed description thereof will be provided in the following description of Example 3.

Figure 3A:
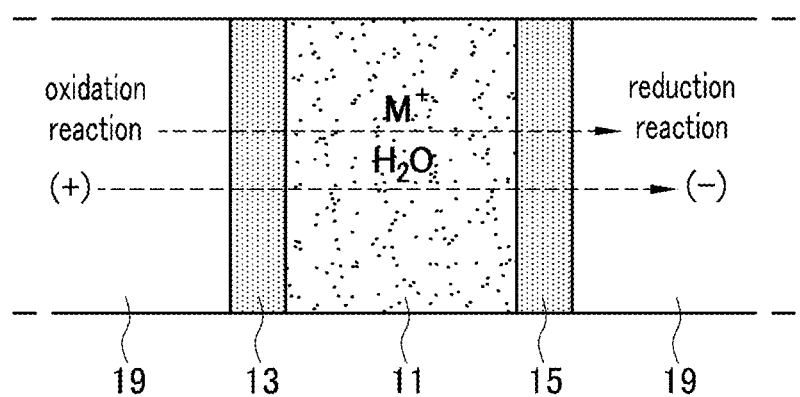
FIG. 3A is a diagram for describing a reversible electrode reaction of the electroosmotic pump according to the first example embodiment.
Figure 3B:
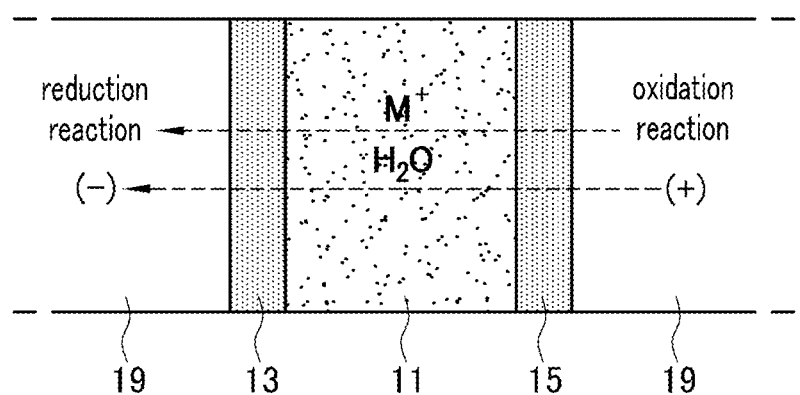
FIG. 3B is a diagram for describing the reversible electrode reaction of the electroosmotic pump according to the first example embodiment.

FIG. 3A and FIG. 3B are diagrams for describing a reversible electrode reaction of the electroosmotic pump according to the first example embodiment.

Either of the first electrode 13 and the second electrode 15 generates cations through an electrochemical reaction, while the other consumes the cations. That is, the conductive polymer contained in each of the first electrode 13 and the second electrode 15 is capable of incurring a reversible electrochemical reaction. Accordingly, both a forward reaction and a reverse reaction can occur in each of the first electrode 13 and the second electrode 15.

For example, referring to FIG. 3A, the first electrode 13 generates cations, whereas the second electrode 15 consumes cations. On the contrary, referring to FIG. 3B, the second electrode 15 generates cations, whereas the first electrode 13 consumes cations.

Such a reversible electrode reaction of the electroosmotic pump 10 may be triggered by supplying voltages to the first electrode 13 and the second electrode 15 while reversing a polarity of each voltage alternately. In this way, by allowing the electrochemical reaction to occur in the forward direction and in the reverse direction repeatedly, a pumping force is continuously generated by repetitive reciprocal movements of a fluid.

Since the first electrode 13 and the second electrode 15 can incur a reversible electrochemical reaction, if the polarity of the voltage applied to each of the first electrode 13 and the second electrode 15 is reversed, and, thus, if the reactions that occur in the first electrode 13 and the second electrode 15 are reversed, a flow of the fluid can be altered to an opposite direction.

To elaborate, as depicted in FIG. 3A, a (+) voltage is applied to the first electrode 13, and a (−) voltage is applied to the second electrode 15. At this time, a fluid (represented by $H_2O$ in FIG. 3A and FIG. 3B) can be moved from the first electrode 13 as a (+) electrode to the second electrode 15 as a (−) electrode. Further, as depicted in FIG. 3B, if the polarities of the voltages applied to the first electrode 13 and the second electrode 15 are reversed, that is, if a (+) voltage is applied to the second electrode 15 and a (−) voltage is applied to the first electrode 13, the fluid can be moved from the second electrode 15 as a (+) electrode to the first electrode 13 as a (−) electrode.

As stated above, by using an electrode material capable of making a reversible electrode reaction as the first electrode 13 and the second electrode 15, and by applying the voltages to the first electrode 13 and the second electrode 15 while revering the polarity of each voltage alternately, a flow of the fluid can be changed. Accordingly, since the electrode reaction takes place in the reverse direction, a state of an electrode active material consumed by the forward reaction when the fluid is flown in the forward direction can be returned back into an original state.

That is, if a voltage or a current in an amount as much as a charge amount used to move the fluid in the forward direction is applied to each of the first electrode 13 and the second electrode 15 in the reverse direction, the same amount of fluid as moved in the forward direction can be moved in the reverse direction. Accordingly, the states of the first electrode 13 and the second electrode 15 can be returned back to initial states.

That is, since each of the first electrode 13 and the second electrode 15 can be reproduced as much as they are consumed, it is possible to prevent the first electrode 13 and the second electrode 15 from being consumed when they are used continuously. As a result, a lifetime of the electroosmotic pump 10 is increased, and it is possible to move a transfer target fluid continuously by using the electroosmotic pump 10.

Figure 4:
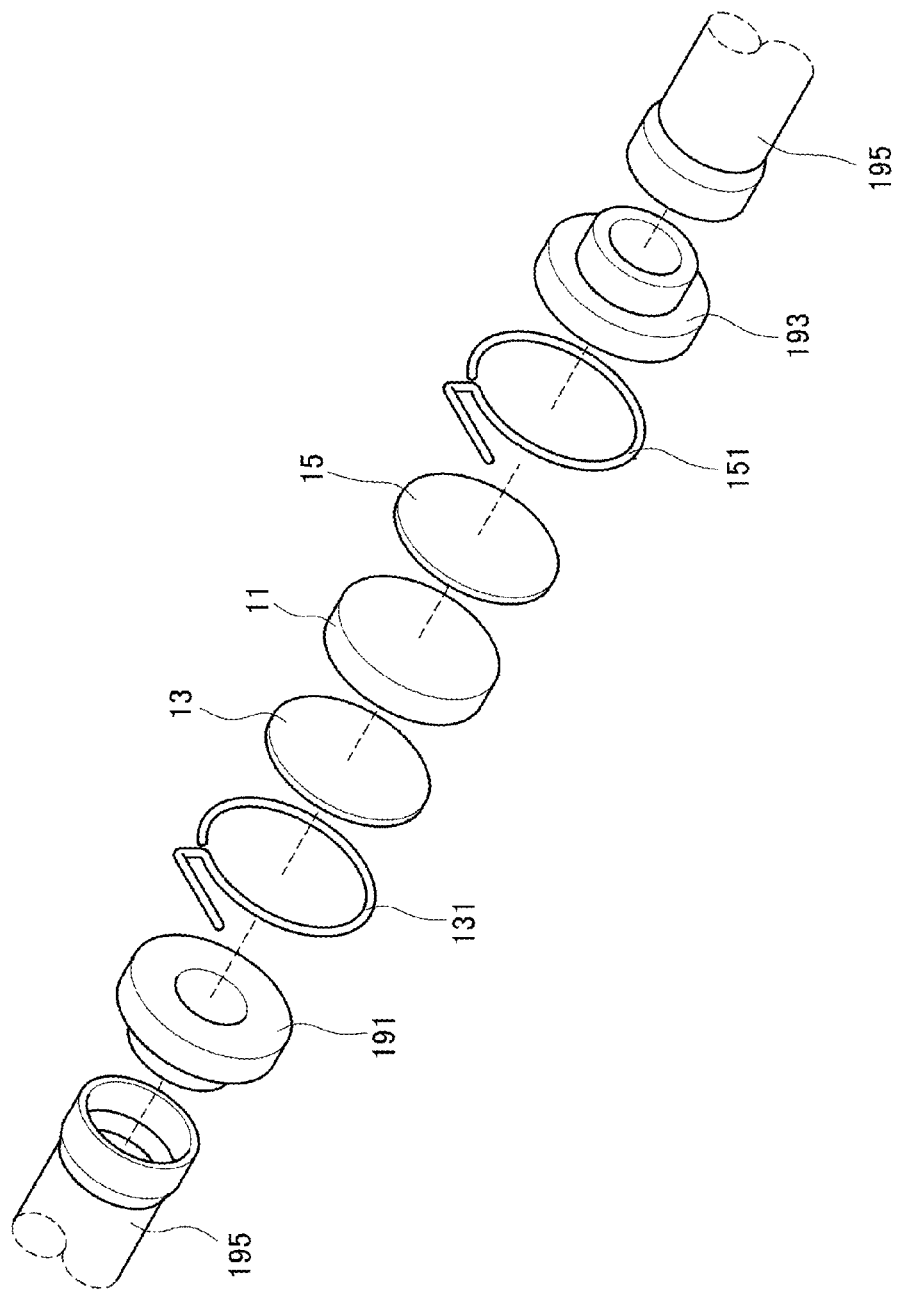
FIG. 4 is an exploded perspective view of the electroosmotic pump according to the first example embodiment.
Figure 5:
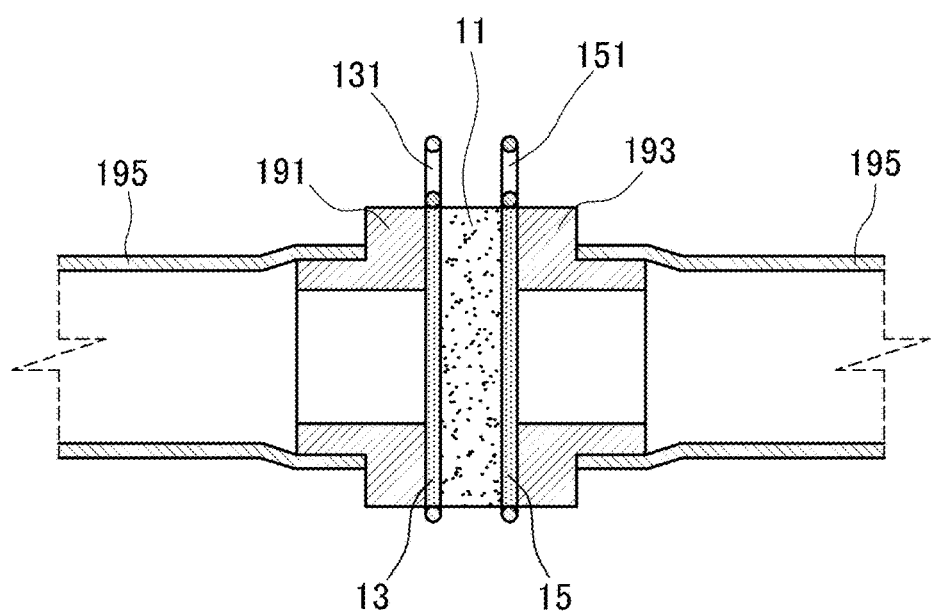
FIG. 5 is a cross sectional view of the electroosmotic pump according to the first example embodiment.

FIG. 4 is an exploded perspective view of the electroosmotic pump according to the first example embodiment, and FIG. 5 is a cross sectional view of the electroosmotic pump shown in FIG. 4.

Referring to FIG. 4 and FIG. 5, the membrane 11 may have a circular plate shape. Here, a coating material, a shield sheet, an adhesive sheet, or the like may be attached to an outer peripheral surface of the membrane 11 to prevent an outflow of a fluid.

Further, each of the first electrode 13 and the second electrode 15 may have a circular plate shape conforming to the shape of the membrane 11, and a coating material, a shield sheet, an adhesive sheet, or the like may also be attached to an outer peripheral surface of each of the first and second electrodes 13 and 15 to prevent an outflow of the fluid.

The fluid path 19 includes a first hollow cap 191 connected to the first electrode 13. Further, the fluid path 19 may also include a second hollow cap 193 connected to the second electrode 15.

An end of the first hollow cap 191 (second hollow cap 193) located on the opposite side from the first electrode 13 (second electrode 15) is connected to a tube 195 in which a fluid can be moved. Here, the tube 195 may be implemented by, by way of non-limiting example, a silicon tube.

Furthermore, the electroosmotic pump 10 further includes a first contact strip 131 fitted to the outer peripheral surface of the first electrode 13 and a second contact strip 151 fitted to the outer peripheral surface of the second electrode 15.

The first contact strip 131 and the second contact strip 151 are connected to the power supply unit 17, and are configured to transmit a voltage or a current to the first electrode 13 and the second electrode 15.

The first contact strip 131 and the second contact strip 151 may be made of a conductive material. For example, the first contact strip 131 and the second contact strip 151 may contain silver (Ag) or copper (Cu), but not limited thereto.

By way of example, the first contact strip 131 and the second contact strip 151 may have a ring shape capable of being fitted around the outer peripheral surfaces of the first electrode 13 and the second electrode 15, as shown in FIG. 4.

Now, the fluid pumping system 1000 according to the first example embodiment will be explained. In the following description, however, the same or similar parts as described above in the electroosmotic pump 10 will be assigned same reference numerals, and redundant description thereof will be simplified or omitted.

FIG. 6 is a configuration view of the fluid pumping system according to the first example embodiment.

The fluid pumping system 1000 includes the electroosmotic pump 10 described above in FIG. 1 to FIG. 5.

As explained above, in the electroosmotic pump 10, a conductive polymer containing anions in the form of large-size polymer, not small mobile anions, is electrodeposited on the first and second electrodes 13 and 15. Accordingly, during an oxidation-reduction reaction of the first and second electrodes 13 and 15, anions cannot move, whereas cations can be moved. Since these cations can easily pass through the negatively charged membrane 11, the velocity of the electrochemical reaction of the first and second electrodes 13 and 15 can be improved in the electroosmotic pump 10. Thus, the electroosmotic pump 10 can have high performance.

The fluid pumping system 1000 is configured to transfer a transfer target fluid from one container to another or to the outside by using a pumping force generated from the electroosmotic pump 10.

Here, the transfer target fluid may include various kinds of fluids such a chemical liquid, an aqueous solution, an organic solution, and so forth, but not limited thereto.

The fluid pumping system 1000 includes a separation member 30. The separation member 30 is provided at least at one end of the electroosmotic pump 10 and is configured to separate a fluid and the transfer target fluid. Further, the separation member 30 also serves to define a space in which the fluid is contained and a space in which the transfer target fluid is contained lest the fluid and the transfer target fluid should be mixed, and also serves to transfer a pumping force generated by a movement of the fluid to the transfer target fluid.

The separation member 30 as stated above may be implemented by an oil forming an oil gap, a diaphragm of a rubber or a metal plate made of a thin film having elasticity, a polymer film, a slider, or the like, but not limited thereto.

As stated earlier, the conductive polymer is capable of incurring a reversible electrochemical reaction. By supplying voltages to the first electrode 13 and the second electrode 15 while reversing a polarity of each voltage alternately, the electrochemical reaction is allowed to take place repeatedly in a forward direction and in a reverse direction alternately. Through these repeated reciprocating movements of the fluid, the pumping force can be generated.

By way of example, the electroosmotic pump 10 is capable of repeatedly transferring a suction force and an expulsive force to the transfer target fluid. If the suction force is transmitted to the transfer target fluid, the transfer target fluid can be discharged into a transfer line 50 from the container 60. If the expulsive force is transmitted to the transfer target fluid, on the other hand, the transfer target fluid can be discharged out to the outside from the transfer line 50. That is, the pumping force generated by the electroosmotic pump 10 may be a suction force and an expulsive force.

Furthermore, as stated before, each of the first electrode 13 and the second electrode 15 contains a conductive polymer material that makes a reversible electrochemical reaction. Accordingly, if voltages are applied to the first electrode 13 and the second electrode 15 while reversing a polarity of each voltage alternately, the first electrode 13 and the second electrode 15 can be reproduced as much as they are consumed. Therefore, the lifetime of the electroosmotic pump 10 can be increased, and a large amount of transfer target fluid can be transferred continuously.

The fluid pumping system 1000 is equipped with the transfer line 50 configured to provide a path through which the transfer target fluid is transferred by the pumping force from the electroosmotic pump 10.

One end of the transfer line 50 is connected to the container 60, and the other end thereof is connected to the outside. With this configuration, the transfer line 50 provides a path through which the transfer target fluid is transferred. By way of non-limiting example, the transfer line 50 may be a pipe or a hose, and may be made of an appropriate material depending on the characteristic of the transfer target fluid.

The fluid pumping system 1000 also includes a first opening/closing member 20 and a second opening/closing member 50 respectively provided at both ends of the transfer line 50 and configured to be opened or closed to allow or block a flow of the transfer target fluid.

That is, each of the first opening/closing member 20 and the second opening/closing member 40 can be opened to allow the fluid to flow therethrough or to be closed to block the flow of the fluid. By way of non-limiting example, each of the first and second opening members 20 and 40 may be implemented by a valve, and, more specifically, may be a check value configured to allow a flow of the fluid only in a single direction.

Here, opened/closed states of the first opening/closing member 20 and the second opening/closing member 40 are opposite to each other. If one of the opening/closing members 20 and 40 is opened, the other is closed.

For instance, if the suction force is transmitted to the transfer target fluid, the first opening/closing member 20 is opened whereas the second opening/closing valve 50 is closed. On the contrary, if the expulsive force is transmitted to the transfer target fluid, the first opening/closing member 20 is closed whereas the second opening/closing member 40 is opened.

Referring to FIG. 6, if the fluid of the electroosmotic pump 10 is moved in a direction ①, the separation member 30 is moved in the direction ① as well. Accordingly, the transfer target fluid is affected by a suction force in a direction whereby it is flown toward the electroosmotic pump 10. At this time, the transfer target fluid that exists within the container 60 needs to be flown out into the transfer line 50, whereas the target fluid once flown to the outside should be prevented from re-entering the transfer line 50. To this end, if the suction force is transmitted to the transfer target fluid, the first opening/closing member 20 is opened, thus allowing the transfer target fluid to be moved from the container 60 into the transfer line 50. At this time, the transfer target fluid is moved in a direction ⓐ. Then, as the second opening/closing valve 40 is closed, the target fluid once discharged to the outside can be prevented from flowing into the transfer line 50 again from the outside.

Furthermore, if voltages having the reverse polarities to those of the voltages applied when the fluid is moved in the direction ① are applied to the first electrode 13 and the second electrode 15, the fluid is moved in a direction ②, and the separation member 30 is also moved in the direction ② by being pushed by the fluid. Accordingly, the transfer target fluid is affected by an expulsive force in a direction whereby it is getting away from the electroosmotic pump 10. At this time, the transfer target fluid that exists within the transfer line 50 needs to be transferred to the outside while it is prevented from re-entering the container 50 after discharged out. To this end, if the expulsive force is transmitted to the transfer target fluid, the second opening/closing member 40 is opened, thus allowing the transfer target fluid to be moved from the transfer line 50 to the outside. At this time, the transfer target fluid is moved in a direction (D. Then, as the first opening/closing valve 20 is closed, the transfer target fluid can be suppressed from flowing back into the container 60 from the transfer line 50.

Here, in case that the first opening/closing member 20 and the second opening/closing member 40 are check valves, by installing the two check valves in opposite directions within the transfer line 50, the above-described operation by the first and second opening/closing valves 20 and 40 (that is, the operation that allows the transfer target fluid to be flown out only in a desired direction) can be easily accomplished.

As described above, the fluid pumping system 1000 transmits a suction force and an expulsive force to the transfer target fluid alternately by repeatedly reversing the polarities of the voltages applied to both ends of the first electrode 13 and the second electrode 15. By allowing or blocking the flow of the transfer target fluid by the first opening/closing member 20 and the second opening/closing member 40, it is possible to continuously transfer the transfer target fluid.

The fluid pumping system 1000 further includes a pumping line 70 configured to transmit the pumping force to the transfer line 50.

The pumping line 70 is branched from a portion of the transfer line 50 between the first opening/closing member 20 and the second opening/closing member 40, and is connected to the electroosmotic pump 10. In this configuration, the pumping line 70 is capable of transmitting the pumping force to both the first opening/closing member 20 and the second opening/closing member 40.

The separation member 30 may be provided within the pumping line 70. With this configuration, the pumping force generated by the electroosmotic pump 10 can be transmitted to the transfer target fluid.

The fluid pumping system 1000 further includes a stopper 80 configured to limit a moving distance of the separation member 30 when the separation member 30 is moved by the movement of the fluid.

By way of example, the stopper 80 is capable of preventing the separation member 30 from being moved to an end portion of the pumping line 70 and falling out. Further, the stopper 80 is also capable of suppressing the separation member 30 from being brought into contact with the electroosmotic pump 10 by being pushed by the transfer target fluid.

The stopper 80 may be provided at each side of the separation member 30. At this time, the stopper 80 located adjacent to the electroosmotic pump 10 prevents suppresses the separation member 30 from being brought into contact with the electroosmotic pump 10, and the stopper 80 located adjacent to the transfer line 50 suppresses the separation member 30 from falling out of the pumping line 70.

As stated above, in the electroosmotic pump 10 and the fluid pumping system 1000 according to the first example embodiment, a conductive polymer containing an anionic polymer (i.e., large-size polymer anions), not the molecular anions, is electrodeposited on the electrodes 13 and 15. Accordingly, when ions are moved to establish a charge balance after an oxidation-reduction reaction of the electrodes 13 and 15, anions cannot be moved whereas cations that exist in the fluid can be moved. Since an attraction force is applied between the cations and the negatively charged membrane 11, the cations can pass through the membrane 11 smoothly. Therefore, the velocity of the electrochemical reaction of the electrodes 13 and 15 can be increased, so that the performance of the electroosmotic pump 10 can be improved.

Furthermore, in the electroosmotic pump 10 and the fluid pumping system 1000, the first electrode 13 and the second electrode 15 contains the conductive polymer capable of incurring a reversible electrochemical reaction. Thus, by applying, to the first electrode 13 and the second electrode 15, voltages of the reverse polarities to those applied previously, an electrode reaction can be made to take place in a reverse direction, so that an electrode active material once consumed when flowing the fluid in the forward direction can be returned back to an original state. Accordingly, in the electroosmotic pump 10 and the fluid pumping system 1000, a large quantity of fluid can be moved for a long time without accompanying gas generation, while maintaining the size and the configuration of the two electrodes 13 and 15 as they were originally. Thus, the electroosmotic pump 10 and the fluid pumping system 1000 have long lifetime and a wide range of applications.

Below, effects of the first example embodiment will be investigated based on various examples and comparative examples. However, it should be noted that the present disclosure is not limited to the following examples.

Example 1

In Example 1, a disc membrane having a thickness of 2 mm and a diameter of 8 mm was used, and this disc membrane was fabricated by using silica in a size of 500 nm. Further, there was used an electrode which was produced by electrodepositing PANI-PSS$^-$ on a disc-shaped porous carbon electrode having a diameter of 8 mm. For the electrodeposition of the PANI-PSS$^-$, there was employed an oxidation-electrodeposition method of circulating a –0.2 V to 1.2 V vs Ag/AgCl at 50 mV/s. To synthesize the PANI-PSS$^-$, aniline of 0.1 M was used as a monomer, and a PSSA (polystyrenesulfonic acid) solution of 0.3 M was used.

Example 2

Example 2 was conducted under the same conditions as those of Example 1 except that PEDOT-PSS$^-$, not the PANI-PSS$^-$, was electrodeposited on a disc-shaped porous carbon electrode. PEDOT was prepared by producing a conductive polymer by using EDOT (3,4-ethylenedioxythiophene) as a monomer.

Example 3

In Example 3, a conductive polymer complex containing CNT (carbon nanotube) was used as an electrode material. An electrode was fabricated as follows. After cleaned in a chloric acid solution, NW-CNT (multiwall carbon nanotube) of 50 mg was put into water having a volume of 90 mL along with a 30%-PSSA solution of 6 mL, and agitated for 24 hours so that the NW-CNT is well dispersed in the solution. Then, an undiluted aniline solution of 0.9 mL was added to the dispersed solution, and, after undergone through an ultrasonic process, the mixture was agitated for one day so that the solutions were well mixed. Thereafter, APS (ammonium peroxysulfate) of 2.2 g was slowly added into the mixed solution while maintaining the mixed solution at 0° C., so that a PANN-PSS-CNT complex was formed and dispersed in the solution. Then, a porous carbon electrode was dip-coated in the solution and dried at a room temperature. By repeating this dip-coating and drying process twice, an electrode coated with the PANI-PSS-CNT complex was obtained.

Comparative Example 1

Comparative example 1 was conducted under the same conditions as those of Example 1 except that PANI-NO$_3^-$, not the PANI-PSS$^-$, was electrodeposited on a disc-shaped carbon electrode. To synthesize the PANI-NO$_3^-$, aniline of 0.1 M was used as a monomer, and a HNO$_3$ solution of 0.3 M was used.

Comparative Example 2

Comparative example 2 was conducted under the same conditions as those of Example 1 except that PANI-SO$_4^{2-}$, not the PANI-PSS$^-$, was electrodeposited on a disc-shaped carbon electrode. To synthesize the PANI-SO$_4^{2-}$, aniline of 0.1 M was used as a monomer, and a H$_2$SO$_4$ solution of 0.3 M was used.

Example 1 vs. Comparative Example 1

A voltage of 1.5 V was applied to both ends of each of an electroosmotic pump including the electrode of Example 1 (i.e., the electrode on which the PANI-PSS$^-$ is electrodeposited) and an electroosmotic pump including the electrode of Comparative example 1 (i.e., the electrode on which the PANI-NO$_3^-$ is electrodeposited). A variation in a current value was observed and a flow velocity was measured for 10 minutes. The variation in the current value is depicted in FIG. 7A, and the measured flow velocity is provided in FIG. 7B.

Figure 7A:
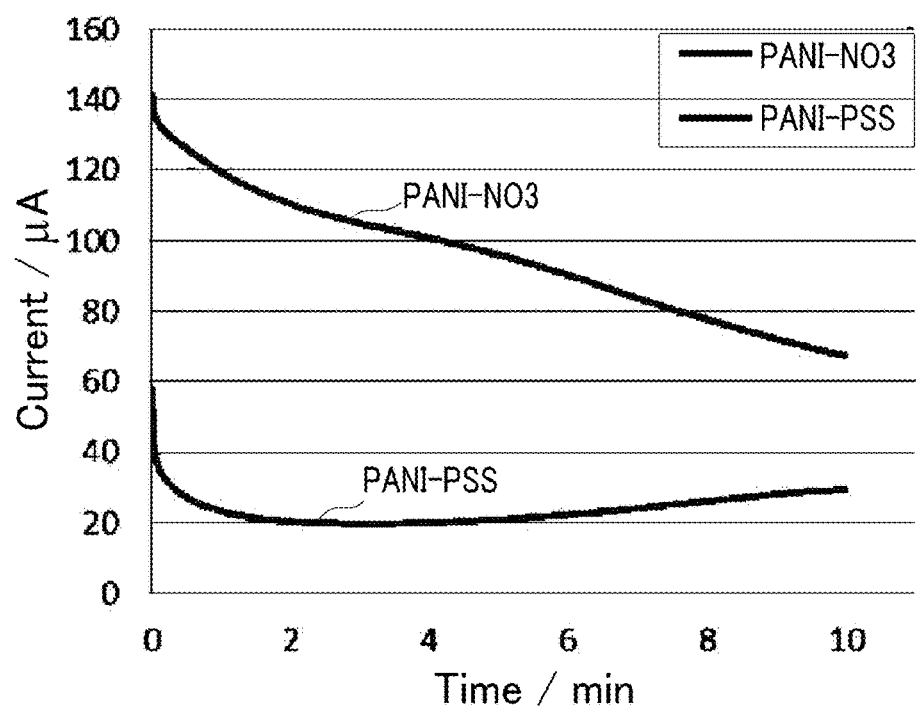
FIG. 7A is a graph showing a comparison of electric current variations of an electroosmotic pump in respective cases of using an electrode containing $PANI-NO_3^-$ and an electroosmotic pump using an electrode containing $PANI-PSS^-$.
Figure 7B:
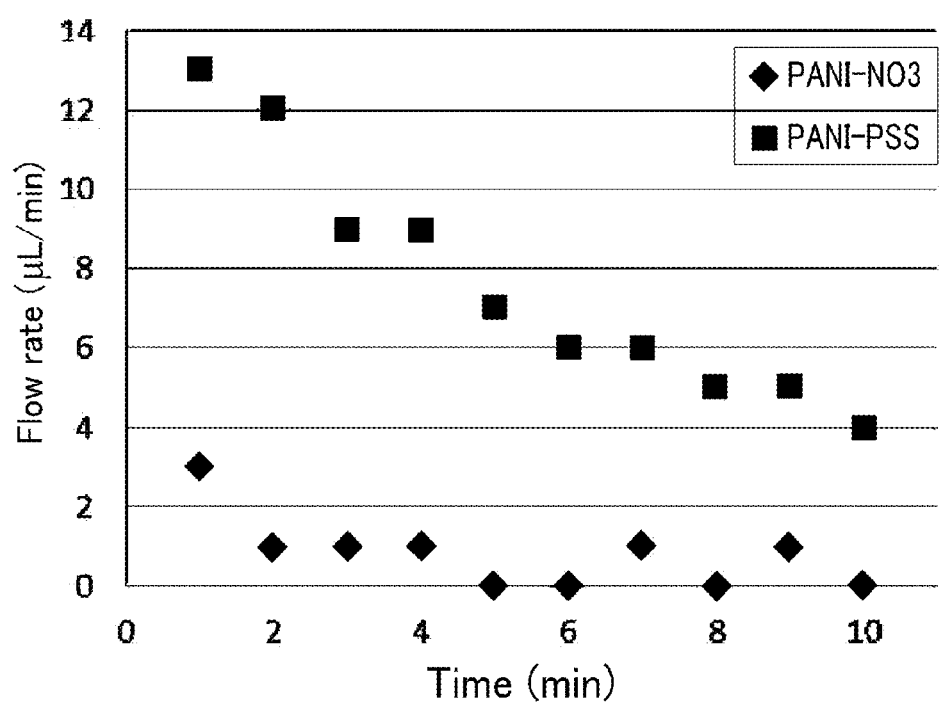
FIG. 7B is a graph showing a comparison of flow rates of the electroosmotic pump in the respective cases of using the electrode containing $PANI-NO_3^-$ and the electrode containing $PANI-PSS^-$.

Referring to FIG. 7A and FIG. 7B, in case of the electroosmotic pump including the electrode on which the PANI-NO$_3^-$ is electrodeposited, although it exhibited a flow velocity of about 3 µL/min at an initial stage, it was observed that the electroosmotic pump had almost lost a function as a pump after 1 minute. Meanwhile, in case of the electroosmotic pump including the electrode on which the PANI-PSS$^-$ is electrodeposited, the electroosmotic pump was observed to be capable of pumping for up to 10 minutes, though a flow velocity thereof was found to decrease slowly after reaching 13 µL/min at an initial stage.

As can be seen from the above results, the electroosmotic pump including the conductive polymer electrode containing the anionic polymer provides much higher pumping performance, as compared to the electroosmotic pump including the conductive polymer electrode containing the small molecular ions.

Figure 8A:
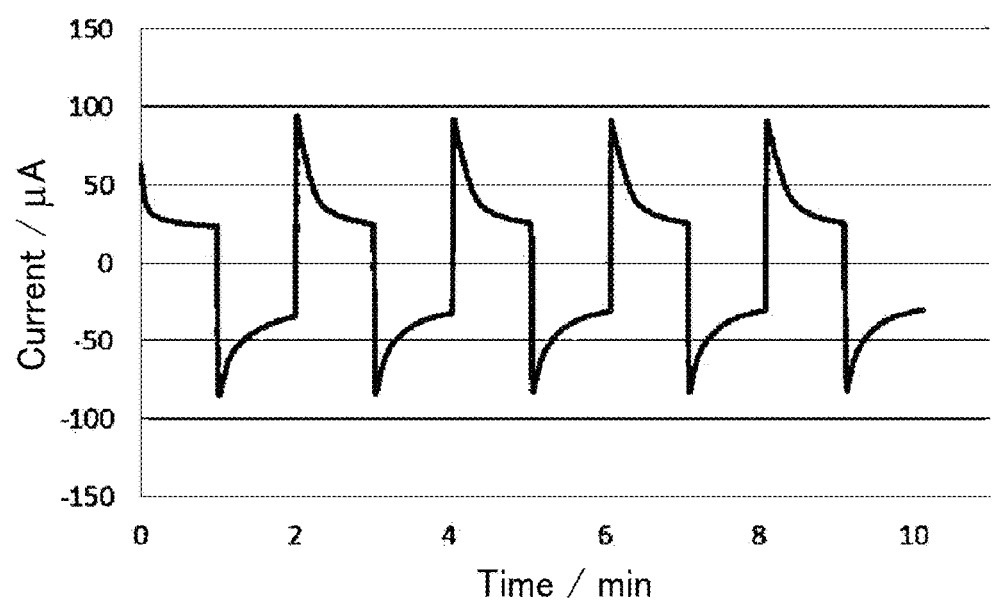
FIG. 8A is a current response graph according to a reversible reaction of an electroosmotic pump using an electrode containing $PANI-NO_3^-$.
Figure 8B:
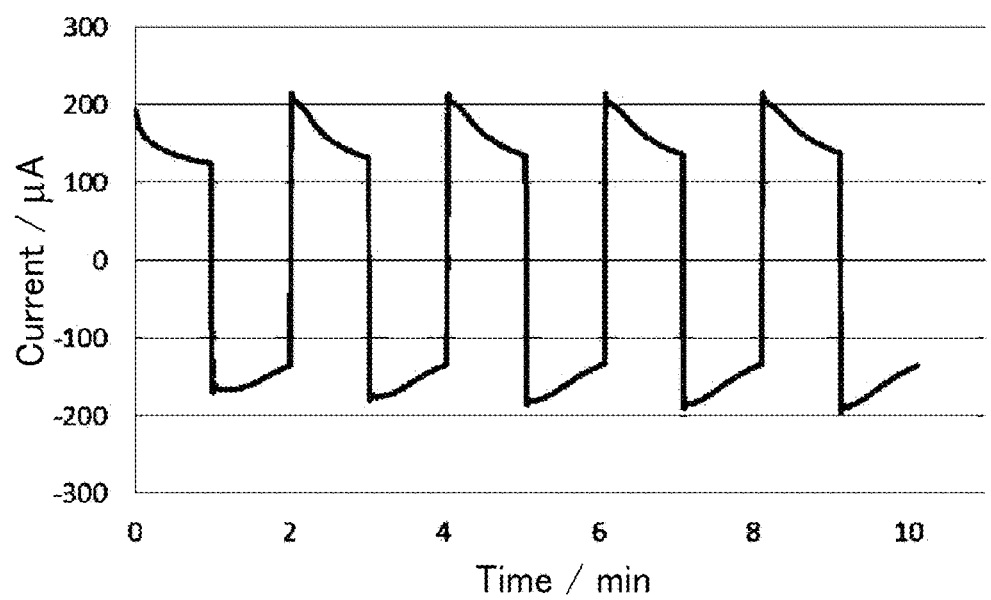
FIG. 8B is a current response graph according to a reversible reaction of an electroosmotic pump using an electrode containing $PANI-PSS^-$.

Further, FIG. 8A is a current response graph obtained when a voltage of 1.5V was applied to each end of the electroosmotic pump according to Comparative example 1 while alternating a polarity of the voltage alternately every one minute, and FIG. 8B is a current response graph obtained when a voltage of 1.5 V was applied to each end of the electroosmotic pump according to Example 1 while alternating a polarity of the voltage every one minute.

Referring to FIG. 8A, in case of the electroosmotic pump including the electrode on which the PANI-NO$_3^-$ was electrodeposited, an electric current of 50 µA or less was found to flow in this electroosmotic pump, and a flow velocity was found to be only 3 μL/min or less. Referring to FIG. 8B, on the other hand, in case of the electroosmotic pump including the electrode on which PANI-PSS⁻ was electrodeposited, an electric current of about 150 μA or less was found to flow in this electroosmotic pump, and a flow velocity of 10 μL/min could be maintained both in a forward direction and in a reverse direction.

As can be seen from the above results, the electroosmotic pump including the conductive polymer electrode containing the anionic polymer has more stable and much higher flow velocity according to electrode reactions in the forward/reverse directions, as compared to the electroosmotic pump including the conductive polymer electrode containing the small molecular ions.

Figure 9:
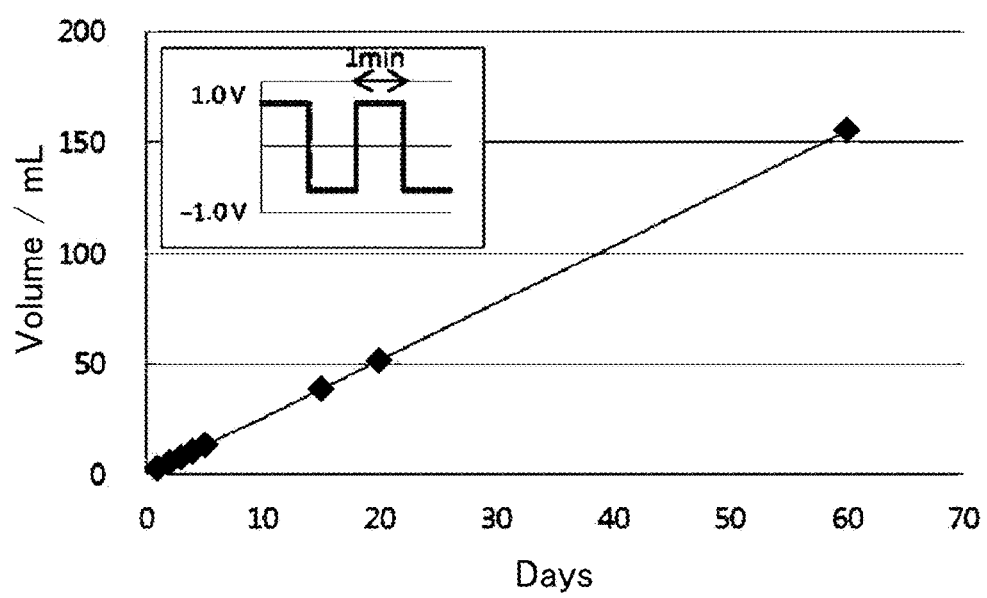
FIG. 9 is a graph showing a lifetime of a fluid pumping system including an electroosmotic pump using an electrode containing $PANI-PSS^-$.

Meanwhile, FIG. 9 is a graph showing a lifetime of a fluid pumping system including an electroosmotic pump using an electrode on which PANI-PSS⁻ is electrodeposited. As depicted in FIG. 9, the fluid pumping system including the electroosmotic pump using the electrode on which the PANI-PSS⁻ is electrodeposited was observed to be operated stably for more than 2 months, during which a transfer target fluid of 150 ml or more could be transferred. That is, as consumption and reproduction of the electrode take place repeatedly, it is possible to use the electroosmotic pump more stably for a longer period of time.

Example 1 vs. Comparative Example 2

Figure 10:
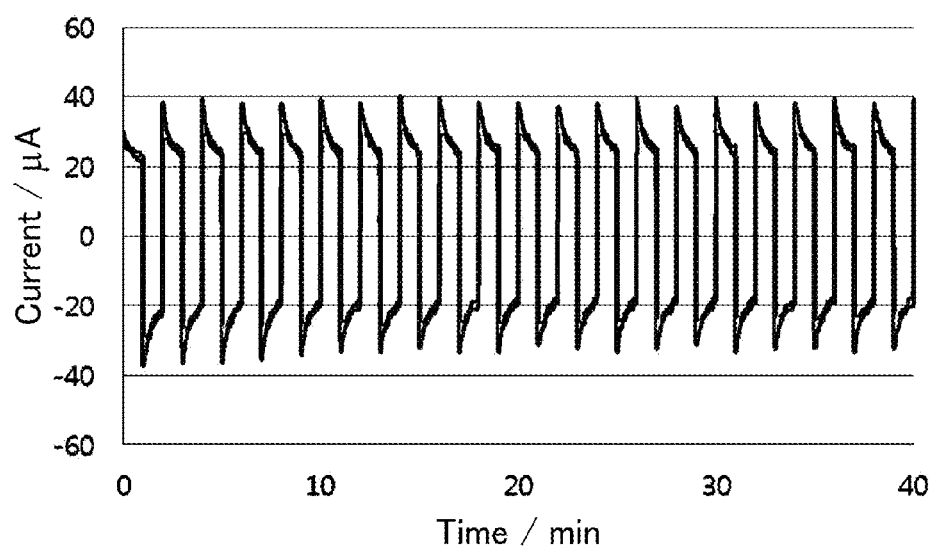
FIG. 10 is a current response graph according to a reversible reaction of an electroosmotic pump using an electrode containing $PANI-SO_4^{2-}$.

FIG. 10 is a current response graph obtained when a voltage of 1.5 V was applied to each electrode (on which the PANI-NO₃⁻ was electrodeposited) of the electroosmotic pump according to Comparative example 2 while reversing a polarity of the voltage every one minute.

Referring to FIG. 10, in case of the electroosmotic pump including the electrodes on which the PANI-NO₃⁻ was electrodeposited, an electric current of 40 μA or less was found to flow in this electroosmotic pump, and a flow velocity was found to be only 3 μL/min or less. That is, the electroosmotic pump including the electrodes on which the PANI-NO₃⁻ was electrodeposited exhibited far lower performance than that of the electroosmotic pump including the electrode on which PANI-PSS⁻ was electrodeposited, in which the electric current of about 150 μA or less was found to flow and a flow velocity was found to be 10 μL/min.

Example 2 vs. Comparative Examples 1 and 2

Figure 11:
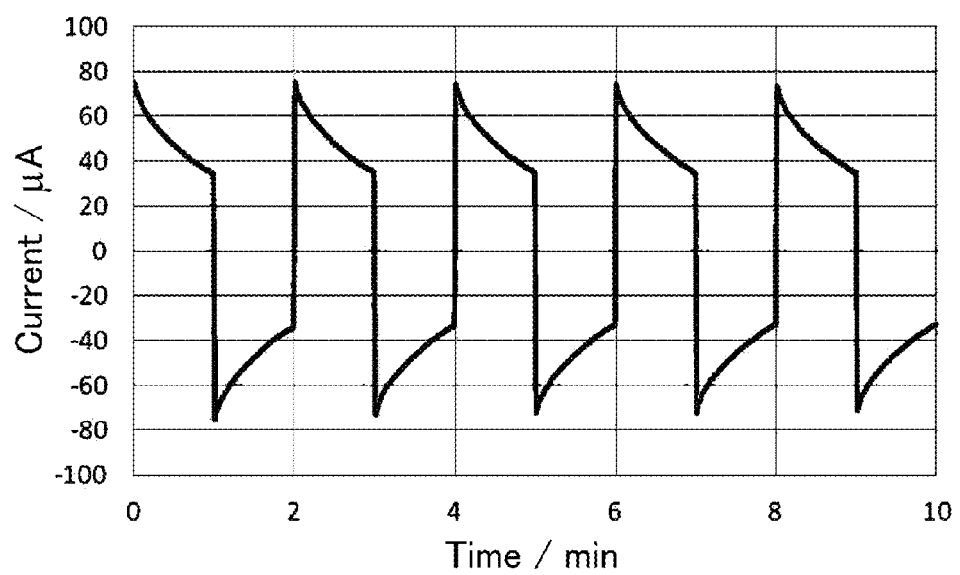
FIG. 11 is a current response graph according to a reversible reaction of an electroosmotic pump using an electrode containing $PEDOT-PSS^-$.

FIG. 11 is a current response graph obtained when a voltage of 1.5 V was applied to each electrode (on which the PEDOT-PSS⁻ was electrodeposited) of the electroosmotic pump according to Example 2 while revering a polarity of the voltage every one minute.

Referring to FIG. 11, in case of the electroosmotic pump including the electrodes on which the PEDOT-PSS⁻ was electrodeposited, an electric current of about 80 μA or less was found to flow in this electroosmotic pump, and a flow velocity was found to be 7 μL/min or less. The magnitude of the current response and the flow velocity in Example 2 ware found to be higher than those of Comparative examples 1 and 2. That is, it is proved that the electrode containing the conductive polymer mixed with the anionic polymer has higher pumping performance, as compared to the electrode containing the conductive polymer mixed with the molecular anions.

Example 3 vs. Examples 1 and 2

Figure 12A:
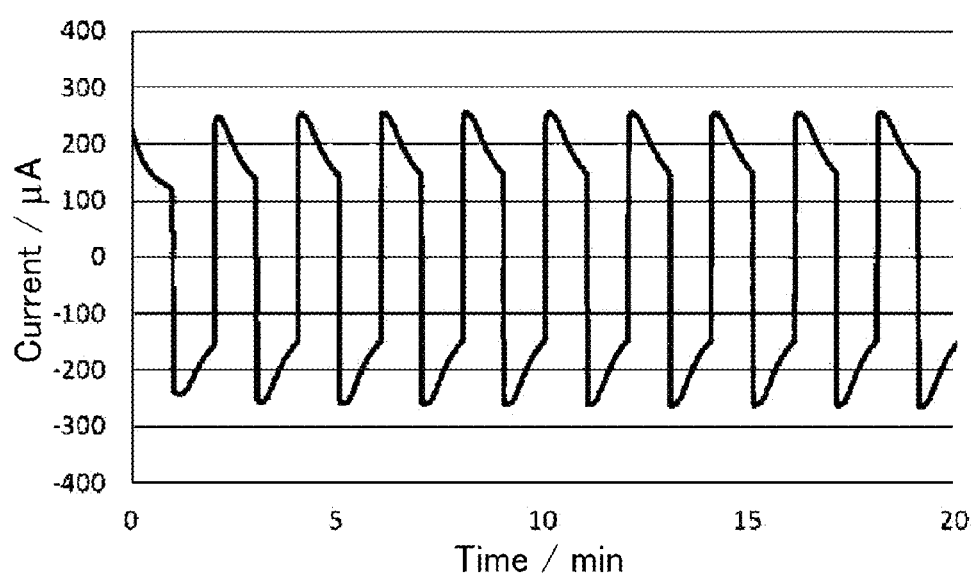
FIG. 12A is a current response graph according to a reversible reaction of an electroosmotic pump using a PANI-PSS-CNT electrode.
Figure 12B:
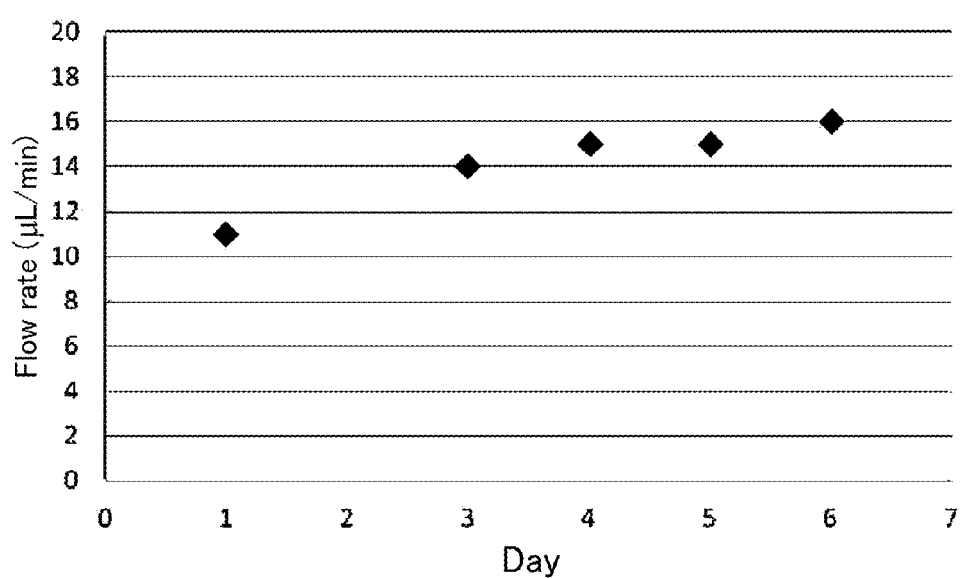
FIG. 12B is a graph showing a flow rate of the electroosmotic pump using the PANI-PSS-CNT electrode.

FIG. 12A and FIG. 12B are graphs showing a current response and a flow velocity, respectively, which were obtained when a voltage of 1.5 V was applied to each electrode (coated with a PANI-PSS-CNT complex) of the electroosmotic pump according to Example 3 while reversing a polarity of the voltage every one minute.

Referring to FIG. 12A, in case of the electroosmotic pump including the electrodes coated with the PANI-PSS-CNT complex, an electric current of about 250 μA or more was found to flow. Further, referring to FIG. 12B, a flow velocity in this electroosmotic pump was found to be about 15 μL/min. As can be seen from these results, the electroosmotic pump of Example 2 exhibits higher magnitude of current response, higher flow velocity and higher pumping performance, as compared to those of the electroosmotic pumps of Examples 1 and 2.

[Electroosmotic Pump and Fluid Pumping System Including Porous Carbon Electrodes]

Now, an electroosmotic pump according to a second example embodiment of the present disclosure will be explained. Here, the same or similar parts as those described in the electroosmotic pump of the first example embodiment will be assigned same reference numerals.

Figure 13:
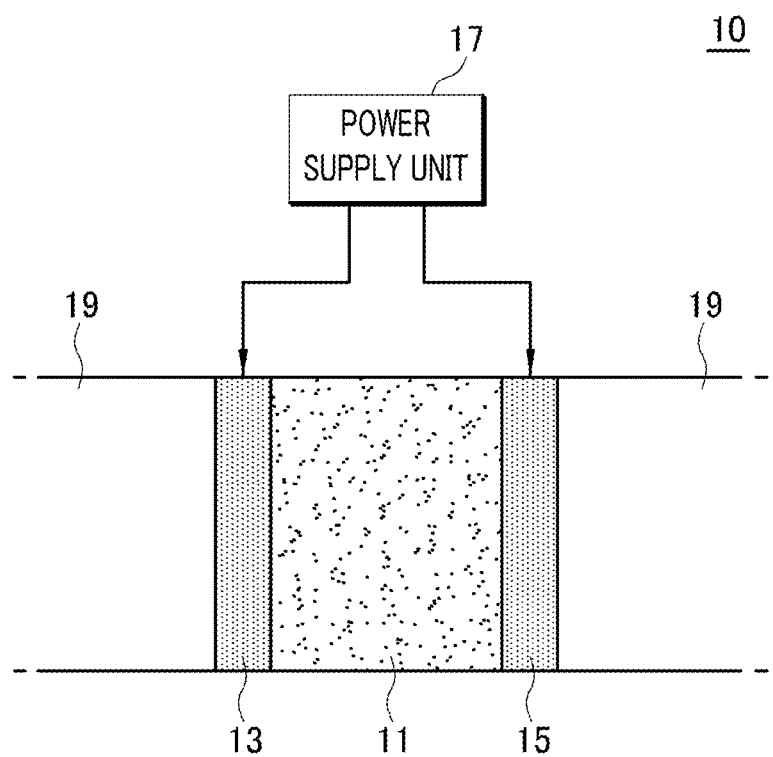
FIG. 13 is a configuration view of an electroosmotic pump according to a second example embodiment.

FIG. 13 is a configuration view illustrating the electroosmotic pump according to the second example embodiment of the present disclosure.

The electroosmotic pump 10 includes a membrane 11; and a first electrode 13 and a second electrode 15 respectively provided at two opposite sides of the membrane 11. The first electrode 13 and the second electrode 15 are connected to a power supply unit 17.

The membrane 11 is provided in a fluid path 19 through which a fluid moves. The membrane 15 is made of a porous material or has a porous structure to allow a fluid to move therethrough.

The first electrode 13 and the second electrode 15 are provided at the two opposite sides of the membrane on the fluid path 19. Each of the first electrode 13 and the second electrode 15 may be made of porous carbon only. The first electrode 13 and the second electrode 15 are maintained spaced apart from each other at a regular interval with the membrane 11 therebetween. Like the membrane 11, each of the first electrode 13 and the second electrode 15 is also made of a porous material or has a porous structure to allow a fluid to flow therethrough.

The power supply unit 17 is connected to the first electrode 13 and the second electrode 15, and is configured to supply a power to the first electrode 13 and the second electrode 15 so that an electrochemical reaction may take place. The electrochemical reaction of the first electrode 13 and the second electrode 15 occurs as cations (positive ions) are moved.

To elaborate, the power supply unit 17 is configured to supply a voltage to the first electrode 13 and the second electrode 15 while reversing a polarity of the voltage alternately. Here, the term "supplying a voltage while reversing a polarity of the voltage alternately" means supplying an electric current in opposite directions alternately.

Accordingly, in the electroosmotic pump 10, through the movement of the fluid, a pumping force can be generated, and, at the same time, consumption and reproduction of the first electrode 13 and the second electrode 15 are performed repeatedly.

By way of non-limiting example, the power supply unit 17 includes a DC power supply device (not shown) configured to supply a DC voltage to each of the first electrode 13 and the second electrode 15. Further, the power supply unit 17 may also include a voltage direction switching device (not shown) configured to switch a polarity of the DC voltage supplied to each of the first electrode 13 and the second electrode 15 alternately at a preset time interval.

Through the above-described configuration, it is possible to continuously reverse the polarity of the voltage applied to each of the first electrode 13 and the second electrode 15 at the preset time interval.

The fluid path 19 provides a moving path of the fluid which moves between two opposite sides (spaces) with the membrane 11 and the first and second electrodes 13 and 15 therebetween.

Here, the fluid path 19 may be in the form of a vessel which is filled with the fluid. By way of example, the fluid path 19 may have a cylinder shape, but not limited thereto.

Further, the fluid may also be charged in the membrane 11 and the first and second electrodes 13 and 15 as well as in the fluid path 19.

Furthermore, the fluid path 19 may have an opening for the transmission of a pumping force. For example, the opening may be formed in either one or both of two opposite spaces separated by the membrane 11, the first electrode 13 and the second electrode 15, to thereby transmit the pumping force generated by the movement of the fluid to the outside. For instance, the opening formed at the fluid path 19 may be connected to a pumping line 70 of a fluid pumping system 1000 depicted in FIG. 18, so that the pumping force can be transmitted to the outside FIG. 14 is a diagram for describing an operation of the electroosmotic pump according to the second example embodiment, and FIG. 15A and FIG. 15B are diagrams for describing a reversible electrode response of the electroosmotic pump according to the second example embodiment.

Figure 14:
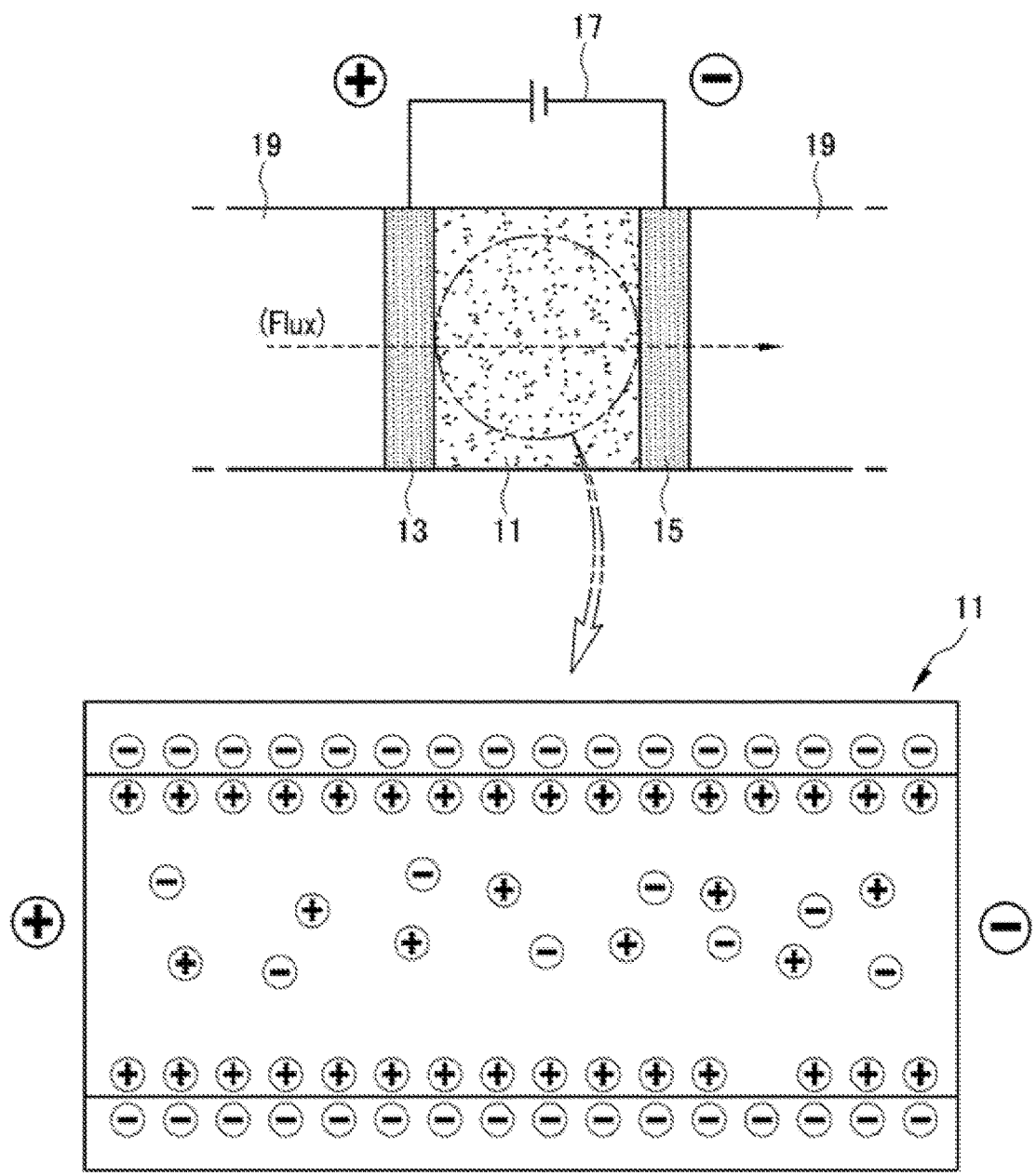
FIG. 14 is a diagram for describing an operation of the electroosmotic pump according to the second example embodiment.
Figure 15A:
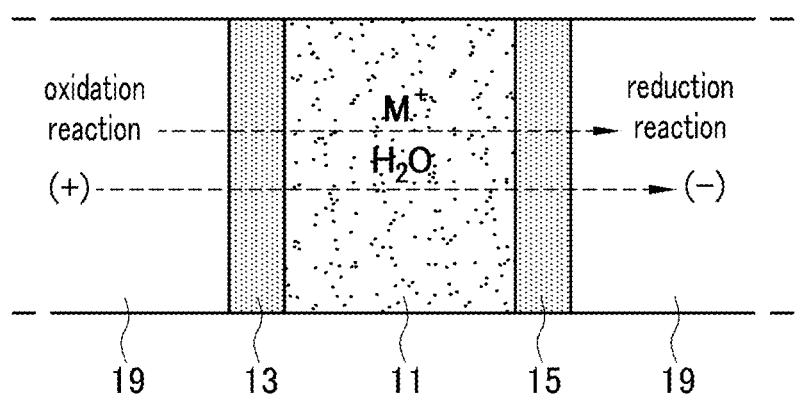
FIG. 15A is a diagram for describing a reversible electrode reaction of the electroosmotic pump according to the second example embodiment.
Figure 15B:
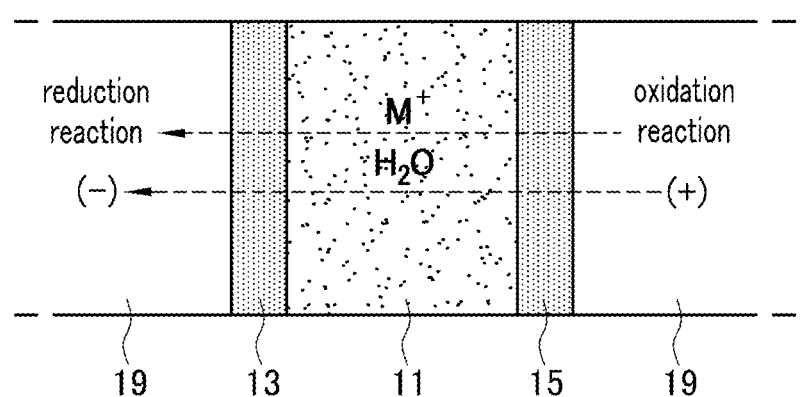
FIG. 15B is a diagram for describing the reversible electrode reaction of the electroosmotic pump according to the second example embodiment.

Referring to FIG. 14, FIG. 15A and FIG. 15B, an operation of the electroosmotic pump 10 according to the second example embodiment will be explained.

If a power is supplied to the first electrode 13 and the second electrode 15 by the power supply unit 17, a voltage difference is generated between the first electrode 13 and the second electrode 15.

Due to the voltage difference between the first electrode 13 and the second electrode 15, an oxidation-reduction reaction takes place in the first electrode 13 and the second electrode 15, so that a charge balance is broken. At this time, as ions which have high mobility are moved, the charge balance is achieved.

Here, if a voltage is applied to each of the first electrode 13 and the second electrode 15, an oxidation-reduction reaction occurs in the first electrode 13 and the second electrode 15, and ions are moved through the membrane 11, so that the fluid can also be moved.

The membrane 11 allows not only the fluid but also ions to move therethrough. If the power supply unit 17 is connected to the electrodes 13 and 15, the fluid and the ions can be moved from one side of the membrane 11 to the other side, or vice versa. As the fluid and the ions are moved through the membrane 11 in this way, a pumping force is generated.

As an example, the membrane 11 may be formed by using silica, glass or the like which is in the form of granules having a size ranging from about 0.1 µm to about 5 µm, but not limited thereto.

Further, for instance, the membrane 11 may be a disc membrane, or a MEA (membrane electrode assembly). Besides these mentioned examples, the membrane 11 may also be formed of various porous materials or may have various porous structures.

An electrochemical reaction of the first electrode 13 and the second electrode 15 occurs as cations (positive ions) are moved in a direction whereby a charge balance is established. Here, either of the first electrode 13 and the second electrode 15 generates cations through the electrochemical reaction, whereas the other of the first electrode 13 and the second electrode 15 consumes the cations through the electrochemical reaction.

Silica, glass, or the like is widely used as a material of the membrane 11. A surface of the membrane made of such a material is negatively charged in an aqueous solution. Here, since there is applied an attraction force between cations and the negatively charged membrane 11, the cations can easily pass through the membrane 11. Accordingly, the velocity of an electrochemical reaction of the electrodes 13 and 15 can be improved. Therefore, movement of the fluid is allowed to take place smoothly, so that the stable electroosmotic pump 10 can be achieved.

Here, the cations generated and consumed during the electrochemical reaction of the first electrode 13 and the second electrode 15 may be monovalent cations, but not limited thereto.

By way of non-limiting example, the cations may include hydrogen ions ($H^+$), but not limited thereto.

An ionic mobility of $H^+$, which is proton, is much higher than those of other cations. As stated above, the electroosmotic pump 10 accompanies a movement of ions and a movement of a fluid. Accordingly, in case that the hydrogen ions are moved during the electrode reaction, a fluid transfer velocity would be increased, so that the performance of the electroosmotic pump 10 can be further ameliorated.

By way of non-limiting example, the electroosmotic pump 10 may use an aqueous solution as the fluid. By using the aqueous solution as the fluid, the hydrogen ions can be moved during the electrode reaction The electroosmotic pump 10 according to the second example embodiment of the present disclosure may exhibit higher pumping performance in a solution which hardly contains electrolyte. At this time, hydrogen ions which are cations generated by dissociation of water may be moved to establish a charge balance.

Further, depending on the fluid involved, the cations may include various ions such as $Na^+$ and $K^+$.

The first electrode 13 and the second electrode 15 are made of porous carbon only. At this time, the fluid is moved through an electrochemical reaction of the porous carbon itself.

The electrochemical reaction of the porous carbon take places as cations are moved in a direction whereby a charge balance of the first electrode 13 and the second electrode 15 is established.

Conventionally, platinum has been widely used as a material of the electrodes. Recently, in order to drive the electroosmotic pump stably without accompanying gas generation, silver (Ag), silver oxide (AgO), MnO(OH), polyaniline (PANI), and the like are used as materials of the electrodes. The electrodes have a basic structure in which the aforementioned electrode materials are coated on a carbon paper by electrodeposition. Conventionally, by using this structure, a pumping force is generated by moving a fluid through an oxidation-reduction reaction of the materials electrodeposited on the electrodes. Since, however, the formation of these conventional electrodes involves a process of electrodepositing another on the carbon paper is required, the whole process of producing the electroosmotic pump has been complicated.

Meanwhile, in the electroosmotic pump 10 according to the second example embodiment of the present disclosure, the first electrode 13 and the second electrode 15 are made of the porous carbon only, and the fluid is moved through the electrochemical reaction of the porous carbon itself. Accordingly, when forming the first and second electrodes 13 and 15, a process of electrodepositing another material can be omitted, and, thus, the electroosmotic pump 10 can be implemented in a simpler way.

Here, the porous carbon may be acid-treated through an oxidation reaction such that oxidizing species exist on a surface thereof.

Accordingly, since various oxidizing species formed on the surface of the porous carbon can participate in an oxidation-reaction reaction, performance of the electroosmotic pump 10 can be improved.

For example, the oxidizing species may include carboxyl, lactone, phenol, quinone, anhydride, and so forth, but not limited thereto.

Here, the surface of the porous carbon may be acid-treated by using various methods including a chemical method and a physical method.

By way of example, the oxidation reaction of the surface of the porous carbon may be implemented by a plasma process. That is, porous carbon may be (acid-treated) oxidized through an oxidation reaction using plasma such that oxidizing species exist on a surface thereof. This plasma oxidation process may be performed by plasma (e.g., air plasma) using various kinds of gasses having an oxidizing power, such as oxygen.

Furthermore, the oxidation reaction may also be incurred by a process using an acidic solution. That is, the porous carbon may be surface-treated through an oxidation reaction in an acidic solution such that oxidizing species exist on a surface thereof. Here, the acidic solution may be a nitric acid solution ($HNO_3$), a sulfuric acid solution ($H_2SO_4$), or a mixture of the nitric acid solution and the sulfuric acid solution, but not limited thereto.

The active species may be differed depending on whether the surface of the porous carbon is treated by the plasma or the like, and, also, depending on a composition of the acidic solution for oxidizing the porous carbon, an oxidation temperature, and so forth.

That is to say, a flow of an electric current and a flow velocity of the pump may be differed depending on a concentration of the acidic solution, a mixture ratio, a reaction temperature, a reaction time, and so forth. Detailed description of this will be provided later when explaining examples of the present disclosure.

FIG. 15A and FIG. 15B are diagrams for describing a reversible reaction of the electroosmotic pump according to the second example embodiment of the present disclosure.

The porous carbon forming the first electrode 13 and the second electrode 15 is capable of incurring a reversible electrochemical reaction. Accordingly, in each of the first electrode 13 and the second electrode 15, both a forward reaction and a reverse reaction can occur.

For example, referring to FIG. 15A, the first electrode 13 generates cations, whereas the second electrode 15 consumes cations. On the contrary, referring to FIG. 15B, the second electrode 15 generates cations, whereas the first electrode 13 consumes cations Such a reversible electrode reaction of the electroosmotic pump 10 may be triggered by supplying voltages to the first electrode 13 and the second electrode 15 while reversing a polarity of each voltage alternately. In this way, by allowing the electrochemical reaction to occur in the forward direction and in the reverse direction repeatedly, a pumping force is continuously generated by repetitive reciprocal movements of a fluid.

Since the first electrode 13 and the second electrode 15 can incur a reversible electrochemical reaction, if the polarity of the voltage applied to each of the first electrode 13 and the second electrode 15 is reversed, and, thus, if the reactions that occur in the first electrode 13 and the second electrode 15 are reversed, a flow of the fluid can be altered to an opposite direction.

To elaborate, as depicted in FIG. 3A, a (+) voltage is applied to the first electrode 13, and a (−) voltage is applied to the second electrode 15. At this time, a fluid (represented by $H_2O$ in FIG. 3A and FIG. 3B) can be moved from the first electrode 13 as a (+) electrode to the second electrode 15 as a (−) electrode. Further, as depicted in FIG. 3B, if the polarities of the voltages applied to the first electrode 13 and the second electrode 15 are reversed, that is, if a (+) voltage is applied to the second electrode 15 and a (−) voltage is applied to the first electrode 13, the fluid can be moved from the second electrode 15 as a (+) electrode to the first electrode 13 as a (−) electrode.

As stated above, by using an electrode material capable of making a reversible electrode reaction as the first electrode 13 and the second electrode 15, and by applying the voltages to the first electrode 13 and the second electrode 15 while revering the polarity of each voltage alternately, a flow of the fluid can be changed. Accordingly, since the electrode reaction takes place in the reverse direction, a state of an electrode active material consumed by the forward reaction when the fluid is flown in the forward direction can be returned back into an original state.

That is, if a voltage or a current in an amount as much as a charge amount used to move the fluid in the forward direction is applied to each of the first electrode 13 and the second electrode 15 in the reverse direction, the same amount of fluid as moved in the forward direction can be moved in the reverse direction. Accordingly, the states of the first electrode 13 and the second electrode 15 can be returned back to initial states.

That is, since each of the first electrode 13 and the second electrode 15 can be reproduced as much as they are consumed, it is possible to prevent the first electrode 13 and the second electrode 15 from being consumed when they are used continuously. As a result, a lifetime of the electroosmotic pump 10 is increased, and it is possible to move a transfer target fluid continuously by using the electroosmotic pump 10

Figure 16:
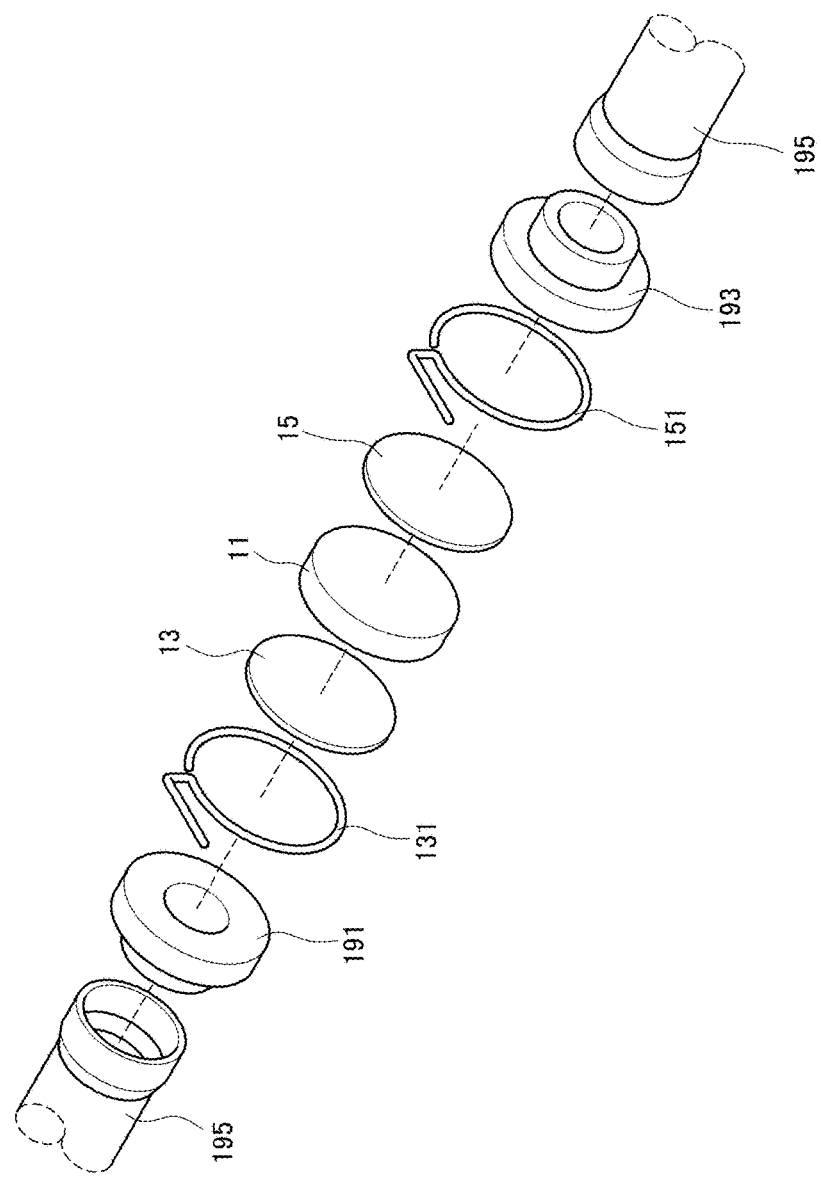
FIG. 16 is an exploded perspective view of the electroosmotic pump according to the second example embodiment.
Figure 17:
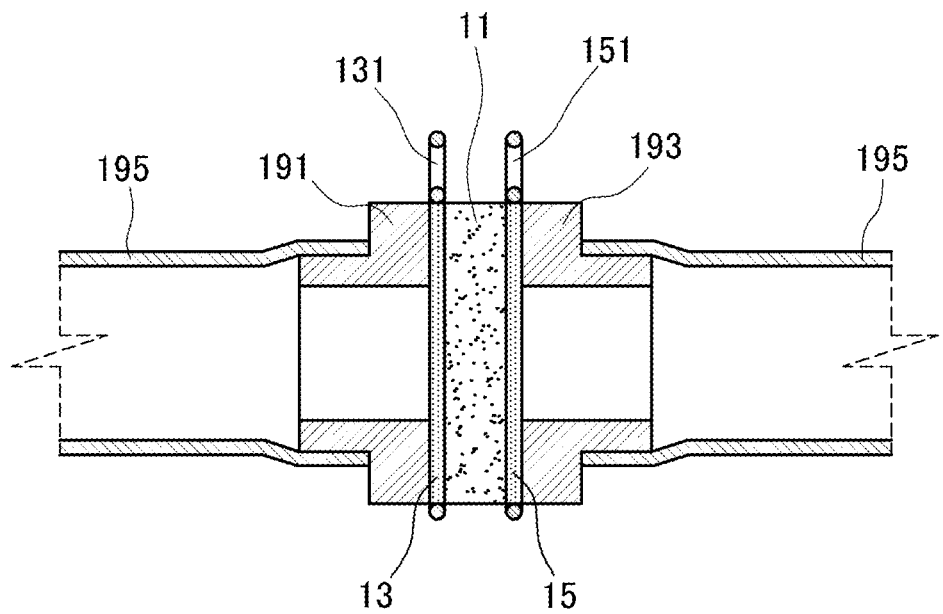
FIG. 17 is a cross sectional view of the electroosmotic pump according to the second example embodiment.

FIG. 16 is an exploded perspective view of the electroosmotic pump according to the second example embodiment, and FIG. 17 is a cross sectional view illustrating the electroosmotic pump shown in FIG. 16.

Referring to FIG. 16 and FIG. 17, the membrane 11 may have a circular plate shape. Here, a coating material, a shield sheet, an adhesive sheet, or the like may be attached to an outer peripheral surface of the membrane 11 to prevent an outflow of a fluid.

Further, each of the first electrode 13 and the second electrode 15 may have a circular plate shape conforming to the shape of the membrane 11, and a coating material, a shield sheet, an adhesive sheet, or the like may also be attached to an outer peripheral surface of each of the first and second electrodes 13 and 15 to prevent an outflow of the fluid The fluid path 19 includes a first hollow cap 191 connected to the first electrode 13. Further, the fluid path 19 may also include a second hollow cap 193 connected to the second electrode 15.

An end of the first hollow cap 191 (second hollow cap 193) located on the opposite side from where the first electrode 13 (second electrode 15) is connected to a tube 195 in which a fluid can be moved.

Here, the tube 195 may be implemented by, by way of non-limiting example, a silicon tube.

Furthermore, the electroosmotic pump 10 further includes a first contact strip 131 fitted to the outer peripheral surface of the first electrode 13 and a second contact strip 151 fitted to the outer peripheral surface of the second electrode 15.

The first contact strip 131 and the second contact strip 151 are connected to the power supply unit 17, and are configured to transmit a voltage or a current to the first electrode 13 and the second electrode 15.

The first contact strip 131 and the second contact strip 151 may be made of a conductive material. For example, the first contact strip 131 and the second contact strip 151 may contain silver (Ag) or copper (Cu), but not limited thereto.

By way of example, the first contact strip 131 and the second contact strip 151 may have a ring shape capable of being fitted around the outer peripheral surfaces of the first electrode 13 and the second electrode 15, as illustrated in FIG. 16.

Now, the fluid pumping system 1000 according to the second example embodiment will be explained. In the following description, however, the same or similar parts as described above in the electroosmotic pumps 10 according to the first and second example embodiment and the fluid pumping system 1000 according to the first example embodiment will be assigned same reference numerals, and redundant description thereof will be simplified or omitted.

Figure 18:
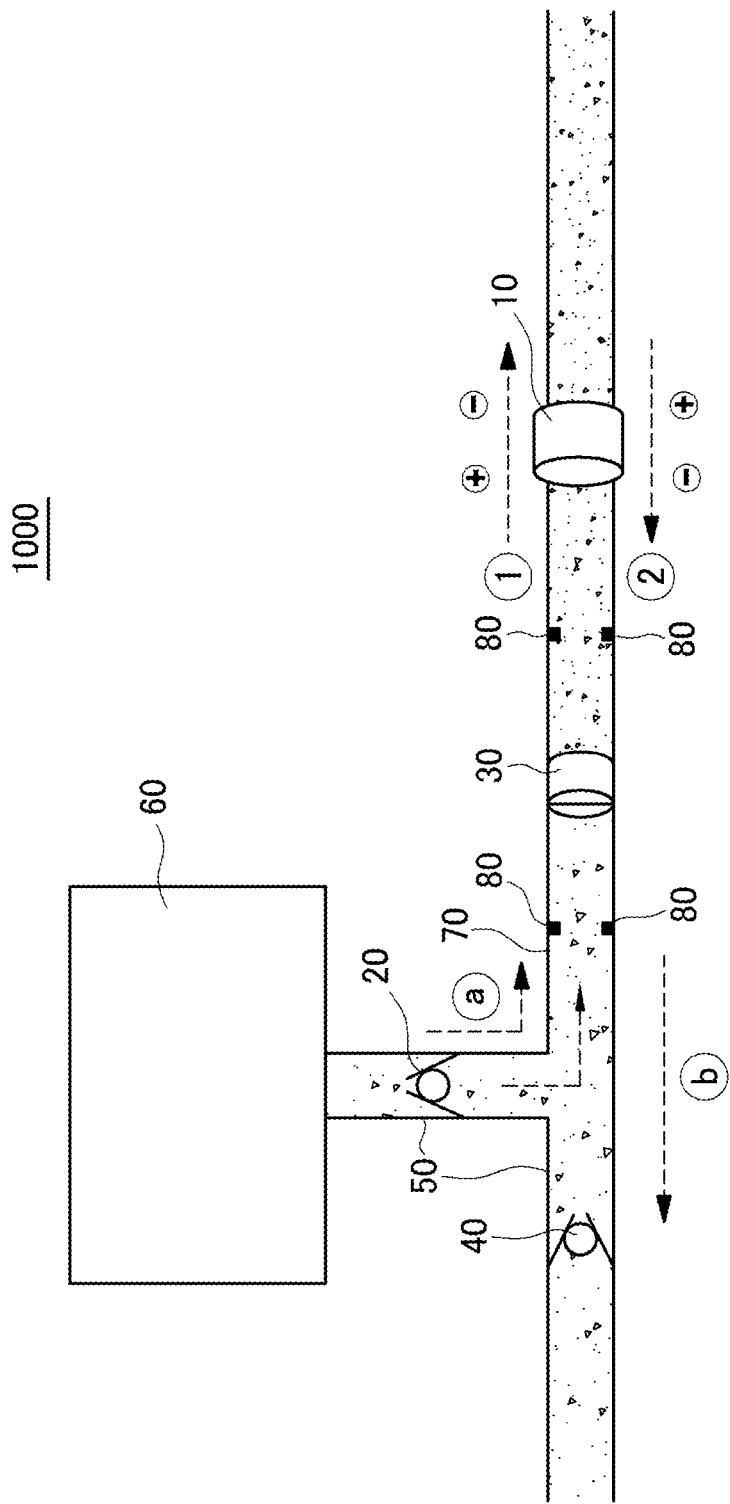
FIG. 18 is a configuration view of a fluid pumping system according to the second example embodiment.

FIG. 18 is a configuration view of the fluid pumping system according to the second example embodiment.

The fluid pumping system 1000 includes the electroosmotic pump 10 described above in FIG. 13 to FIG. 17.

As explained above, in the electroosmotic pump 10, since the first electrode 13 and the second electrode 15 are made of porous carbon only, a process of electrodepositing another material on the electrodes can be omitted when forming the electrodes. Therefore, it is possible to produce the electroosmotic pump 10 in a simpler way.

The fluid pumping system 1000 is configured to transfer a transfer target fluid from one container to another or to the outside by using a pumping force generated from the electroosmotic pump 10.

Here, the transfer target fluid may include various kinds of fluids such a chemical liquid, an aqueous solution, an organic solution, and so forth, but not limited thereto.

The fluid pumping system 1000 includes a separation member 30. The separation member 30 is provided at least at one end of the electroosmotic pump 10 and is configured to separate a fluid and the transfer target fluid.

Further, the separation member 30 also serves to define a space in which the fluid is contained and a space in which the transfer target fluid is contained lest the fluid and the transfer target fluid should be mixed, and also serves to transfer a pumping force generated by a movement of the fluid to the transfer target fluid.

The separation member 30 as stated above may be implemented by an oil forming an oil gap, a diaphragm of a rubber or a metal plate made of a thin film having elasticity, a polymer film, a slider, or the like, but not limited thereto.

As stated earlier, the porous carbon is capable of incurring a reversible electrochemical reaction. By supplying voltages to the first electrode 13 and the second electrode 15 while reversing a polarity of each voltage alternately, the electrochemical reaction is allowed to take place repeatedly in a forward direction and in a reverse direction alternately. Through these repeated reciprocating movements of the fluid, the pumping force can be generated.

By way of example, the electroosmotic pump 10 is capable of repeatedly transferring a suction force and an expulsive force to the transfer target fluid. If the suction force is transmitted to the transfer target fluid, the transfer target fluid can be discharged into a transfer line 50 from the container 60. If the expulsive force is transmitted to the transfer target fluid, on the other hand, the transfer target fluid can be discharged out to the outside from the transfer line 50. That is, the pumping force generated by the electroosmotic pump 10 may be a suction force and an expulsive force.

Furthermore, as stated before, each of the first electrode 13 and the second electrode 15 contains porous carbon that makes a reversible electrochemical reaction. Accordingly, if voltages are applied to the first electrode 13 and the second electrode 15 while reversing a polarity of each voltage alternately, the first electrode 13 and the second electrode 15 can be reproduced as much as they are consumed. Therefore, the lifetime of the electroosmotic pump 10 can be increased, and a large amount of transfer target fluid can be transferred continuously.

The fluid pumping system 1000 is equipped with the transfer line 50 configured to provide a path through which the transfer target fluid is transferred by the pumping force from the electroosmotic pump 10.

One end of the transfer line 50 is connected to the container 60, and the other end thereof is connected to the outside. With this configuration, the transfer line 50 provides a path through which the transfer target fluid is transferred. By way of non-limiting example, the transfer line 50 may be a pipe or a hose, and may be made of an appropriate material depending on the characteristic of the transfer target fluid.

The fluid pumping system 1000 also includes a first opening/closing member 20 and a second opening/closing member 50 respectively provided at both ends of the transfer line 50 and configured to be opened or closed to allow or block a flow of the transfer target fluid.

That is, each of the first opening/closing member 20 and the second opening/closing member 40 can be opened to allow the fluid to flow therethrough or to be closed to block the flow of the fluid. By way of non-limiting example, each of the first and second opening members 20 and 40 may be implemented by a valve, and, more specifically, may be a check value configured to allow a flow of the fluid only in a single direction.

Here, opened/closed states of the first opening/closing member 20 and the second opening/closing member 40 are opposite to each other. If one of the opening/closing members 20 and 40 is opened, the other is closed.

For instance, if the suction force is transmitted to the transfer target fluid, the first opening/closing member 20 is opened whereas the second opening/closing valve 50 is closed. On the contrary, if the expulsive force is transmitted to the transfer target fluid, the first opening/closing member 20 is closed whereas the second opening/closing member 40 is opened Referring to FIG. 18, if the fluid of the electroosmotic pump 10 is moved in a direction ①, the separation member 30 is moved in the direction ① as well. Accordingly, the transfer target fluid is affected by a suction force in a direction whereby it is flown toward the electroosmotic pump 10. At this time, the transfer target fluid that exists within the container 60 needs to be flown out into the transfer line 50, whereas the target fluid once flown to the outside should be prevented from re-entering the transfer line 50. To this end, if the suction force is transmitted to the transfer target fluid, the first opening/closing member 20 is opened, thus allowing the transfer target fluid to be moved from the container 60 into the transfer line 50. At this time, the transfer target fluid is moved in a direction ⓐ. Then, as the second opening/closing valve 40 is closed, the target fluid once discharged to the outside can be prevented from flowing into the transfer line 50 again from the outside.

Furthermore, if voltages having the reverse polarities to those of the voltages applied when the fluid is moved in the direction ① are applied to the first electrode 13 and the second electrode 15, the fluid is moved in a direction ②, and the separation member 30 is also moved in the direction ② by being pushed by the fluid. Accordingly, the transfer target fluid is affected by an expulsive force in a direction whereby it is getting away from the electroosmotic pump 10. At this time, the transfer target fluid that exists within the transfer line 50 needs to be transferred to the outside while it is prevented from re-entering the container 50 after discharged out. To this end, if the expulsive force is transmitted to the transfer target fluid, the second opening/closing member 40 is opened, thus allowing the transfer target fluid to be moved from the transfer line 50 to the outside. At this time, the transfer target fluid is moved in a direction ⓑ. Then, as the first opening/closing valve 20 is closed, the transfer target fluid can be suppressed from flowing back into the container 60 from the transfer line 50.

Here, in case that the first opening/closing member 20 and the second opening/closing member 40 are check valves, by installing the two check valves in opposite directions within the transfer line 50, the above-described operation by the first and second opening/closing valves 20 and 40 (that is, the operation that allows the transfer target fluid to be flown out only in a desired direction) can be easily accomplished.

As described above, the fluid pumping system 1000 transmits a suction force and an expulsive force to the transfer target fluid alternately by repeatedly reversing the polarities of the voltages applied to both ends of the first electrode 13 and the second electrode 15. By allowing or blocking the flow of the transfer target fluid by the first opening/closing member 20 and the second opening/closing member 40, it is possible to continuously transfer the transfer target fluid.

The fluid pumping system 1000 further includes a pumping line 70 which is branched from a portion of the first opening/closing member 20 and the second opening/closing member 40 and is connected to the electroosmotic pump 10. The pumping line 70 is configured to transmit the pumping force to the transfer line 50.

Since the pumping line 70 is branched from the portion of the transfer line 50 between the first opening/closing member 20 and the second opening/closing member 40, the pumping line 70 is capable of transmitting the pumping force to both the first opening/closing member 20 and the second opening/closing member 40.

The separation member 30 may be provided within the pumping line 70. With this configuration, the pumping force generated by the electroosmotic pump 10 can be transmitted to the transfer target fluid.

The fluid pumping system 1000 further includes a stopper 80 configured to limit a moving distance of the separation member 30 when the separation member 30 is moved by the movement of the fluid.

By way of example, the stopper 80 is capable of preventing the separation member 30 from being moved to an end portion of the pumping line 70 and falling out. Further, the stopper 80 is also capable of suppressing the separation member 30 from being brought into contact with the electroosmotic pump 10 by being pushed by the transfer target fluid.

The stopper 80 may be provided at each side of the separation member 30. At this time, the stopper 80 located adjacent to the electroosmotic pump 10 prevents suppresses the separation member 30 from being brought into contact with the electroosmotic pump 10, and the stopper 80 located adjacent to the transfer line 50 suppresses the separation member 30 from falling out of the pumping line 70.

As described above, in the electroosmotic pump 10 and the fluid pumping system 1000 according to the second example embodiment of the present disclosure, the first electrode 13 and the second electrode 15 are formed of porous carbon only, and a pumping force is generated by an electrochemical reaction of the porous carbon itself. Accordingly, when forming the first and second electrodes 13 and 15, a process of electrodepositing another material can be omitted, so that the electroosmotic pump 10 can be produced in a simpler way.

Furthermore, in the electroosmotic pump 10 and the fluid pumping system 100, since the first electrode 13 and the second electrode 15 are formed of porous carbon of which surface is acid-treated by using plasma or an acidic solution, more stable and improved pumping performance can be achieved.

Furthermore, in the electroosmotic pump 10 and the fluid pumping system 1000, the first electrode 13 and the second electrode 15 contains the porous carbon capable of incurring a reversible electrochemical reaction. Thus, by applying, to the first electrode 13 and the second electrode 15, voltages of the reverse polarities to those applied previously, an electrode reaction can be made to take place in a reverse direction, so that an electrode active material once consumed when flowing the fluid in the forward direction can be returned back to an original state. Accordingly, in the electroosmotic pump 10 and the fluid pumping system 1000, a large quantity of fluid can be moved for a long time without accompanying gas generation, while maintaining the size and the configuration of the two electrodes 13 and 15 as they were originally. Thus, the electroosmotic pump 10 and the fluid pumping system 1000 have long lifetime and a wide range of applications.

Below, effects of the second example embodiment will be investigated based on various examples and comparative examples. However, it should be noted that the present disclosure is not limited to the following examples.

Example 1

In Example 1, a disc membrane formed by using silica of 300 nm and having a thickness of 2 mm and a diameter of 8 mm was used as a membrane, and a Spectracarb 2050A carbon paper having a thickness of 0.25 mm and a density of 0.5 g/cm$^3$ was used as electrodes.

Example 2

Example 2 was conducted under the same conditions as those of Example 1 except that the carbon paper of Example 1 was oxidized by air plasma for 10 minutes.

Example 3

Example 3 was conducted under the same conditions as those of Example 1 except that the carbon paper of Example 1 was oxidized in a solution containing sulfuric acid of 95% and nitric acid of 60% at a ratio of 1:1 for about 6 hours while maintaining a temperature of 60° C.

Results of Examples 1, 2 and 3

A voltage of 1.5 V was applied to both ends of each of electroosmotic pumps of Examples 1, 2 and 3 while reversing a polarity of the voltage every one minute. Current response graphs as results of the experiments are provided in FIG. 19, FIG. 20 and FIG. 21A.

Figure 19:
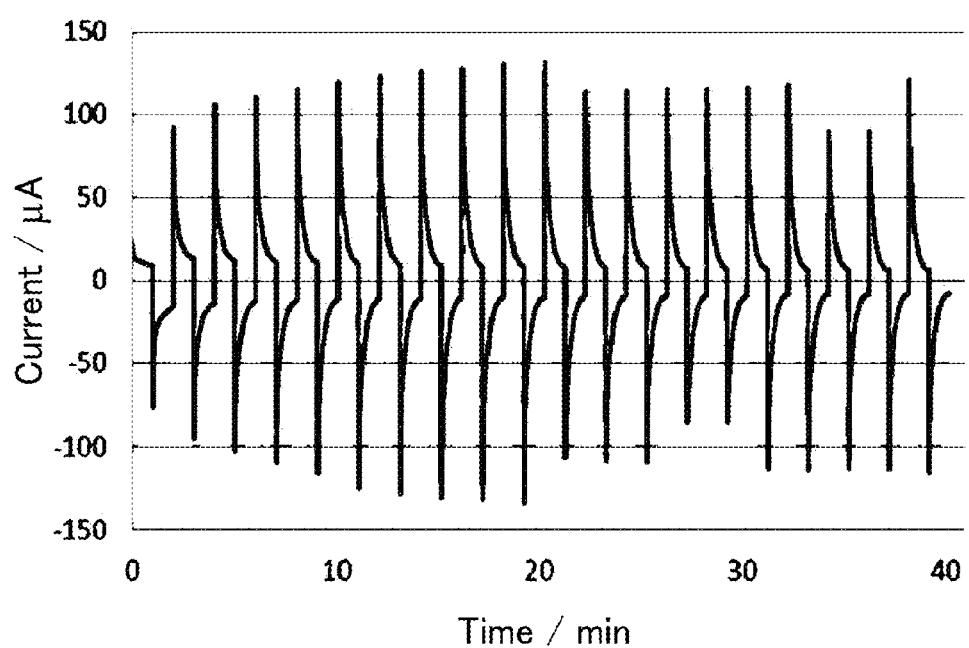
FIG. 19 is a current response graph of an electroosmotic pump using a carbon paper as an electrode without performing an additional treatment on the carbon paper.

First, referring to FIG. 19, in case of the electroosmotic pump using the carbon paper as electrodes without performing any additional treatment on the carbon paper, an electric current of 50 μA or less was found to flow therein, and a fluid movement was also observed. As can be seen from this result, by using the electrodes formed of only the porous carbon, a fluid can be moved through an electrochemical reaction of porous carbon itself.

Figure 20:
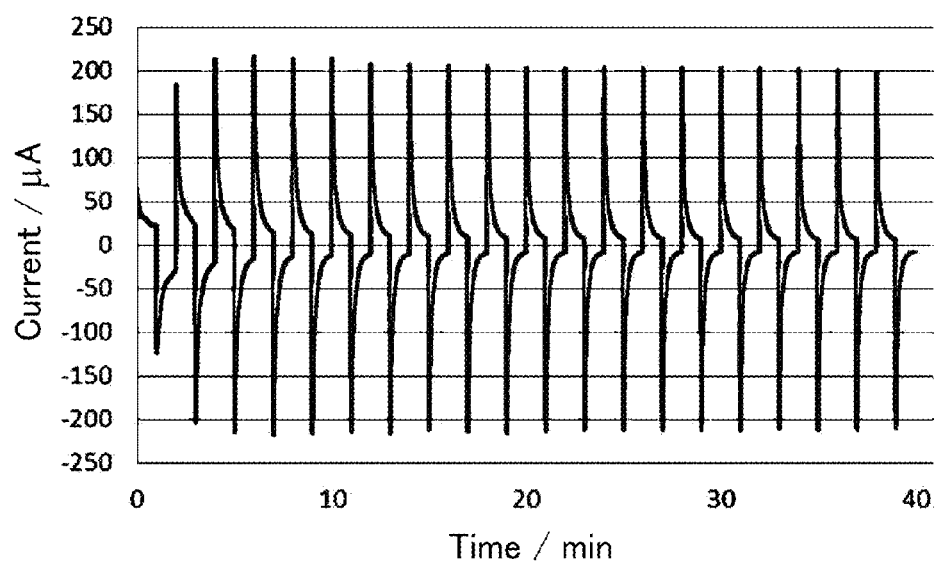
FIG. 20 is a current response graph of an electroosmotic pump using a plasma-processed carbon paper as an electrode.

Referring to FIG. 20, in case of the electroosmotic pump using the carbon paper which was surface-treated by the air plasma, an electric current of about 200 μA was found to flow therein, and a fluid movement was also observed. As can be seen from this result, if the surface of the porous carbon is surface-treated by the plasma, higher pumping performance can be achieved, as compared to the case of using the porous carbon without performing any surface treatment thereon.

Figure 21A:
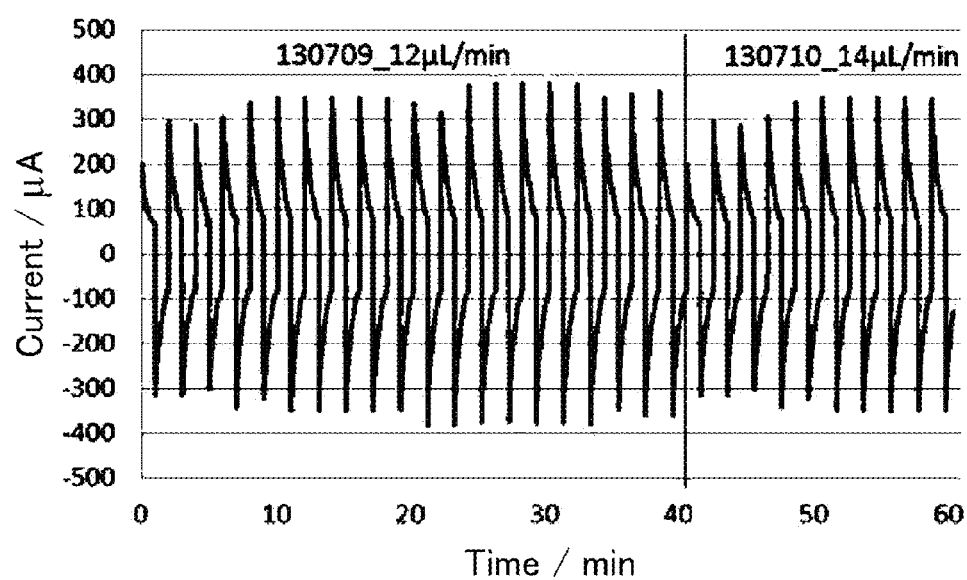
FIG. 21A is a current response graph of an electroosmotic pump using a carbon paper as an electrode by processing the carbon paper in a solution of sulfuric acid and nitric acid (at a ratio of 1:1).
Figure 21B:
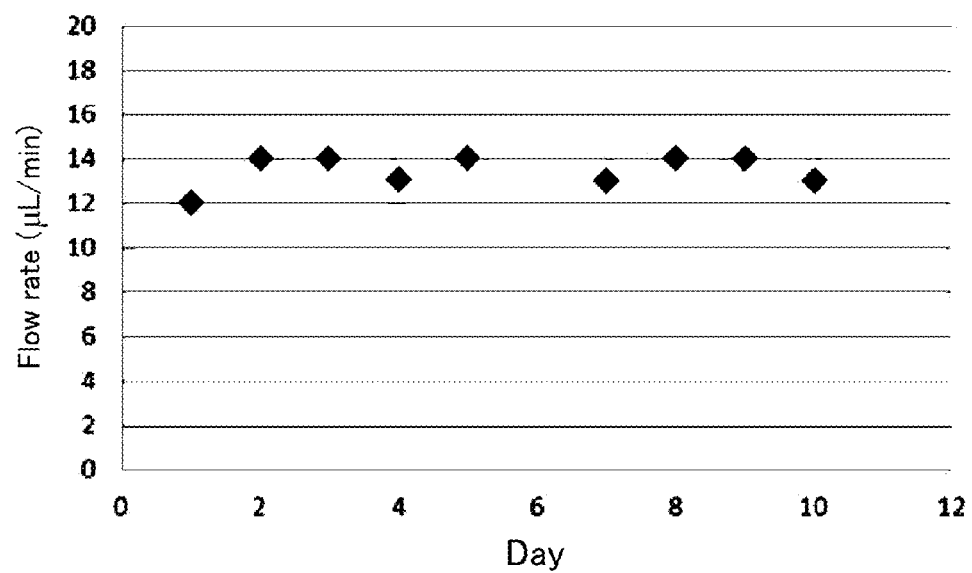
FIG. 21B is a graph showing a flow rate of the electroosmotic pump using the carbon paper as an electrode by processing the carbon paper in the solution of sulfuric acid and nitric acid (at a ratio of 1:1).

Referring to FIG. 21A and FIG. 21B, in case of the electroosmotic pump using the carbon paper oxidized in the solution containing the sulfuric acid of 95% and the nitric acid of 60% at a ratio of 1:1 at the temperature of 60° C. for about 6 hours, an electric current approximate to about 400 μA was found to flow therein, and a flow rate was found to be 14 μL/min. That is, as can be seen from this result, the electrodes formed of the porous carbon on the surface of which oxidizing species are formed through an oxidization reaction has higher pumping performance, as compared to Examples 1 and 2.

Meanwhile, there was conducted another experiment where the carbon paper (CP) was oxidized under different conditions from those of Example 3 while varying a ratio of nitric acid/sulfuric acid, a temperature, a heating time, and so forth. Then, a current flow and a flow rate of the pump were observed in each case, and a comparison result is provided in the following Table 1. In Table 1, nitric acid of 60% and sulfuric acid of 95% were used.

TABLE 1

| Sample | Sulfuric Acid:Nitric Acid (Volume ratio) | Rxn Temperature and time | Flow rate (μL/min) at 1.5 V | Current Initial (μA) | Current After 1 min (μA) |
|---|---|---|---|---|---|
| Untreated CP | | | 2 | 118 | 8 |
| Acid treated CP | 1:3 | 90° C., 12 h | 3 | 44 | 7 |
| Acid treated CP | 1:1 | 90° C., 12 h | 15 | 197 | 94 |
| Acid treated CP | 3:1 | 60° C., 6 h | 15 | 170 | 114 |
| Acid treated CP | 1:1 | 60° C., 10 h | 15 | 260 | 190 |

As can be seen from Table 1, the acid-treated carbon papers have higher pumping performances, as compared to that of the untreated carbon paper. Further, it is also found out that the flow rate of the pump and the current flow vary depending on the conditions for oxidizing the carbon paper. That is, by oxidizing the carbon paper under various conditions, performance of the carbon paper as an electrode can be improved.

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the illustrative embodiments. It shall be understood that all modifications and embodiments conceived from the meaning and scope of the claims and their equivalents are included in the scope of the inventive concept.

We claim:

1. A fluid pumping system, comprising:
   an electroosmotic pump comprising a membrane that allows a fluid to move therethrough;
   a first electrode and a second electrode which are respectively provided at two opposite sides of the membrane, and each of which is formed of a porous material or has a porous structure to allow a fluid to move therethrough,
   a separation member provided on at least one end of the electroosmotic pump, and configured to separate the fluid and a transfer target fluid,
   a transfer line configured to provide a path through which the transfer target fluid is transferred by the pumping force received from the electroosmotic pump, and
   a first opening/closing member near a first end of the transfer line that is connected to a transfer target fluid source and a second opening/closing member provided near a second end of the transfer line that is connected to the outside of the fluid pumping system, and configured to allow or block a flow of the target transfer fluid,
   wherein each of the first electrode and the second electrode contains a conductive polymer in which an anionic polymer is included,
   wherein the conductive polymer incurs a reversible electrochemical reaction, and
   the electrochemical reaction of the first electrode and the second electrode takes place as a cation is moved in a direction whereby a charge balance is established.

2. The electroosmotic pump of claim 1,
   wherein the conductive polymer is formed through polymerization of a monomer in a solution containing the anionic polymer.

3. The electroosmotic pump of claim 1,
   wherein the cation exists in the fluid as a result of dissociation of the fluid.

4. The electroosmotic pump of claim 1,
   wherein one of the first electrode and the second electrode generates a cation through the electrochemical reaction, whereas the other of the first electrode and the second electrode consumes the cation through the electrochemical reaction.

5. The electroosmotic pump of claim 4,
   wherein the cation includes a monovalent cation.

6. The electroosmotic pump of claim 5,
wherein the cation includes a hydrogen ion ($H^+$).

7. The electroosmotic pump of claim 1,
wherein the conductive polymer includes one selected from the group consisting of polyaniline, polypyrrole, polythiophene, polythionine, quinone polymer, derivatives thereof, and combinations thereof.

8. The electroosmotic pump of claim 1,
wherein the anionic polymer includes one selected from the group consisting of polystyrene sulfonate, SPEEK (sulfonated-polyetheretherketone), polyacrylate, polyvinylphosphonate, polyoxometalate, nafion, derivatives thereof, and combinations thereof.

9. The electroosmotic pump of claim 1,
wherein each of the first electrode and the second electrode includes a carbon nanostructure.

10. The electroosmotic pump of claim 9,
wherein the carbon nanostructure includes one or more of a carbon nanotube (CNT), graphene, a carbon nanoparticle, fullerene, and graphite.

11. The electroosmotic pump of claim 1,
wherein the electrochemical reaction is allowed to occur in a forward direction and in a reverse direction repeatedly by supplying a voltage to each of the first electrode and the second electrode while reversing a polarity of the voltage alternately, thus generating a pumping force through repeated reciprocating movements of the fluid, and
each of the first electrode and the second electrode is consumed and reproduced repeatedly by the electrochemical reaction that occurs in the forward direction and in the reverse direction repeatedly.

12. The electroosmotic pump of claim 11, further comprising:
a power supply unit configured to supply a voltage to each of the first electrode and the second electrode while reversing a polarity of the voltage alternately.

13. The electroosmotic pump of claim 12,
wherein the power supply unit includes:
a DC power supply unit configured to supply a DC voltage to each of the first electrode and the second electrode; and
a voltage direction switching device configured to alternately reverse, at a preset time interval, a polarity of the DC voltage which is supplied to each of the first electrode and the second electrode.

14. The fluid pumping system of claim 1,
wherein the electroosmotic pump is configured to generate the pumping force through repeated reciprocating movements of the fluid by transmitting a suction force and an expulsive force to the transfer target fluid repeatedly through the separation member.

15. The fluid pumping system of claim 1, further comprising:
a pumping line branched from a portion of the transfer line between the first opening/closing member and the second opening/closing member, and connected to the electroosmotic pump, and configured to transmit the pumping force to the transfer line.

16. The fluid pumping system of claim 15,
wherein opening and closing of the first opening/closing member is opposite to opening and closing of the second opening/closing member.

17. The fluid pumping system of claim 16,
wherein if the suction force is transmitted to the transfer target fluid, the first opening/closing member is opened whereas the second opening/closing member is closed, and
if the expulsive force is transmitted to the transfer target fluid, the first opening/closing member is closed whereas the second opening/closing member is opened.

* * * * *